US011744813B2

(12) United States Patent
King et al.

(10) Patent No.: US 11,744,813 B2
(45) Date of Patent: Sep. 5, 2023

(54) MODIFIER SYSTEM FOR COMPOSITIONS CONTAINING LAYERED DOUBLE HYDROXIDE

(71) Applicant: OXFORD PHARMASCIENCE LIMITED, Camden London (GB)

(72) Inventors: Elizabeth King, Calne (GB); Marcelo Leonardo Bravo Cordero, Oxford (GB); Ann Taylor-Hutchinson, Hucknall (GB)

(73) Assignee: Oxford Pharmascience Limited, Camden London (GB)

( * ) Notice: Subject to any disclaimer, the term of this patent is extended or adjusted under 35 U.S.C. 154(b) by 0 days.

(21) Appl. No.: 17/519,068

(22) Filed: Nov. 4, 2021

(65) Prior Publication Data

US 2022/0054437 A1    Feb. 24, 2022

Related U.S. Application Data

(63) Continuation of application No. 16/343,812, filed as application No. PCT/GB2017/053237 on Oct. 27, 2017, now abandoned.

(30) Foreign Application Priority Data

Oct. 27, 2016    (GB) ..................................... 1618204

(51) Int. Cl.

| | |
|---|---|
| A61K 31/192 | (2006.01) |
| A61K 47/02 | (2006.01) |
| A61K 47/10 | (2017.01) |
| A61K 47/20 | (2006.01) |
| A61K 47/24 | (2006.01) |
| A61K 47/52 | (2017.01) |

(52) U.S. Cl.
CPC ............ *A61K 31/192* (2013.01); *A61K 47/02* (2013.01); *A61K 47/10* (2013.01); *A61K 47/20* (2013.01); *A61K 47/24* (2013.01); *A61K 47/52* (2017.08)

(58) Field of Classification Search
CPC .......... A61K 33/26; A61K 9/00; A61K 47/48; A61K 9/14; A61K 7/42; A61K 9/0053; A61K 9/16
USPC .......................................... 424/646; 423/600
See application file for complete search history.

(56) References Cited

U.S. PATENT DOCUMENTS

| | | | |
|---|---|---|---|
| 5,641,813 A | 6/1997 | Franklin | |
| 8,062,667 B2 | 11/2011 | Mehta | |

FOREIGN PATENT DOCUMENTS

| | | |
|---|---|---|
| EP | 1341556 | 3/2017 |
| WO | 02/47729 | 6/2002 |

OTHER PUBLICATIONS

Kim et al., "Polymer Coated CaAl-Layered Double Hydroxide Nanomaterials for Potential Calcium Supplement." International Journal of Molecular Sciences 2014, 15, 22563-22579. Published Dec. 5, 2014. (Year: 2014).*
Office Action issued for Chinese Application No. 201780080688.0, dated Feb. 23, 2022.
Zhao Ji-Kuan, et al., Preparation of Mg2Al Layered Double Hydroxide Nanosheets from Triton X-100 Hexagonal Lyotropic Liquid Crystal and Their Application as Drug Carriers, Acta Phys.-Chim. Sin. 2015, 31 (6), 1199-1206.
International Search Report and Written Opinion dated Jan. 11, 2018, from International Application No. PCT/IB2017/053237, 15 pages.
Zhao, C. et al. "Improvement of pharmacokinetic and antitumor activity of layered double hydroxide nanoparticles by coating with PEGylated phospholipid membrane", International Journal of Nanomedicine, Oct. 1, 2014, pp. 4867.
Miao, Y. et al. "Electrospun fibers of layered double hydroxide/biopolymer nanocomposites as effective drug delivery systems", Materials Chemistry and Physics, vol. 134, No. 2, Mar. 23, 2012, pp. 623-630.
Rojas, R. et al. "Modeling drug release from a layered double hydroxide-ibuprofen complex", Applied Clay Science, vol. 62-63, Jul. 1, 2012, pp. 15-20.
Khan, I. et al. "Intercalation and controlled release of pharmaceutically active compounds from a layered double hydroxide", Chemical Communications, 2001, pp. 2342-2343.
Rojas, R. et al. "Structural and physiochemical aspects of drug release from layered double hydroxides and layered hydroxide salts", Applied Clay Science, 109-110 (2015) pp. 119-126.
Nalawade, P. et al. "Layered double hydroxides: A review", Journal of Scientific & Industrial Research, 2009, pp. 267-272.
Prevot, V. et al. "Aerosol-assisted self-assebly of hybrid layered double hydroxide particles in sphericle architectures", Journal of Colloid and Interface science, vol. 356, 2011, pp. 566-572.
Chitrakar et al. "Synthesis of novel layered double hydroxides and its anion exchange properties", Jounal of Hazardous Materials, vol. 185, No. 2-3, 2011, pp. 1435-1439.
Examination Report under Section 18(3) issued in connection with corresponding United Kingdom Patent Application No. GB1618204. 0, dated Mar. 26, 2020 (3 pages).
Examination Report under Sections 12 & 13 of the Patents Act, 1970 and the Patent Rules, 2003, issued in connection with corresponding Indian Patent Application No. 201917020347, dated Dec. 16, 2021 (7 pages).

(Continued)

*Primary Examiner* — Walter E Webb
(74) *Attorney, Agent, or Firm* — Meunier Carlin & Curfman LLC

(57) ABSTRACT

The invention relates to a composition comprising: i) one or more LDH-active anion materials comprising an LDH matrix intercalated with one or more active anions, and ii) a modifier system comprising a) one or more surfactants, in combination with b) one or more compounds having the generic formula MA, where M comprises one or more positively charged ions and A comprises one or more negatively charged counter ions.

14 Claims, 29 Drawing Sheets

(56) References Cited

OTHER PUBLICATIONS

Examination Report issued in connection with correspnding UK Application No. GB1618204.0, dated Mar. 2, 2022, 5 pages.
"Sodium Laurilsulfate used as an excipient" European Medicines Agency, Committee for Human Medicinal Products (CHMP), Oct. 9, 2017, 18 pages.
Office Action issued in connection with corresponding Indian Application No. 201917020347, dated Nov. 16, 2022.
Office Action issued in connection with corresponding Chinese Application No. 201780080688.0, dated Sep. 21, 2022.
Nie et al. "Synthesis and Characterization of Ifosfamide Intercalated Layered Double Hydroxides", Journal of Dispersion Science and Technology, vol. 33, No. 1-3, pp. 339-345 (2012).

* cited by examiner

FIGURE 28

| Surfactants | Sodium Carbonate | 0mg (CONTROL) pH | 0mg % Solubility | 0mg Solvent Method | 50mg pH | 50mg % Solubility | 50mg Solvent Method | 100mg pH | 100mg % Solubility | 100mg Solvent Method | 150mg pH | 150mg % Solubility | 150mg Solvent Method | 200mg pH | 200mg % Solubility | 200mg Solvent Method | 300mg pH | 300mg % Solubility | 300mg Solvent Method |
|---|---|---|---|---|---|---|---|---|---|---|---|---|---|---|---|---|---|---|---|
| None (CONTROL) | 0mg | 2 | 1 | 65 | 2.8 | 3 | | 6.2 | 8 | | 7.2 | 13 | | 7.6 | 15 | | 8.8 | 25 | 41 |
| | 0mg FREE IBU ACID | | 0 | 95 | | | | | | | | | | 6.48 | 57.03 | | | | |
| SLS | 50mg | NT | NT | NT | 3.9 | 2 | NT | 6.9 | 18 | 30 | | | | 9.1 | 30 | 88 | 8.1 | 23 | |
| | 100mg | 4.3 | 1 | NT | 6.4 | 13 | 27 | 6.9 | 26 | 36 | | | | 8.9 | 43 | 87 | | | |
| | 150mg | | | | 6.6 | 38 | 21 | 7 | 36 | 61 | 7 | 44 | | | | | | | |
| | 200mg | 5.3 | 48 | 59 | 6.4 | 48 | | | | | | | | 9.3 | 57 | 88 | 7.8 | 46 | |
| | 300mg | | 2 | 56 | | | | | | | | | | | | | | | |
| Lecithin | 50mg | 2.4 | 2 | | NT | NT | NT | 4.7 | 1 | 30 | | | | 7.4 | 12 | 85 | | | |
| | 100mg | | | | 4.2 | 1 | 27 | 6.1 | 2 | 34 | | | | 8 | 12 | 79 | | | |
| | 150mg | 2.3 | 2 | 62 | | | | | | | | | | | | | | | |
| | 200mg | | | | 4.6 | 1 | 30 | 7.1 | 4 | 55 | | | | 7.4 | 10 | 82 | | | |
| | 300mg | 4.2 | 1 | 64 | | | | 6.5 | 12 | 30 | | | | 8.8 | 28 | 79 | | | |
| Poloxamer 407 | 50mg | 3.2 | 7 | 67 | NT | NT | NT | | | | | | | | | | | | |
| | 60mg | 1.71 | 2.20 | 59.77 | | | | 5.2 | 8 | 30 | | | | 6.6 | 14 | 79 | | | |
| | 60mg FREE IBU ACID | 1.55 | 4.19 | | | | | 6.8 | 15 | 24 | | | | 8.2 | 16 | | | | |
| | 100mg | 3.70 | 3.46 | 64.48 | 4.5 | 12 | NT | | | | | | | | | | | | |
| | 100mg FREE IBU ACID | 1.56 | 7.35 | | | | | 5.9 | 35 | 98 | | | | | | | | | |
| | 150mg | 3.4 | 19 | 65 | | | | | | | | | | | | 79 | | | |
| | 200mg | 3.23 | 20.73 | 63.75 | 4.6 | 14 | | 6.9 | 20 | 24 | | | | 8.4 | 18 | 77 | | | |
| | 200mg FREE IBU ACID | 1.47 | 10.06 | | | | | | | | | | | | | 56 | | | |
| | 300mg | 3.6 | 23 | 77 | | | | | | | | | | | | 94 | | | |
| | 300mg | | | 25 | | | | | | | | | | | | | | | |

FIGURE 29

| ACTIVE PHARMACEUTICAL INGREDIENT (API) TESTED | API Dose | Surfactants | Sodium Carbonate content | 0mg pH | 0mg Solubility | 0mg Solvent Method | 13.56mg pH | 13.56mg Solubility | 13.56mg Solvent Method | 100mg pH | 100mg Solubility | 100mg Solvent Method | 200mg pH | 200mg Solubility | 200mg Solvent Method | 250mg pH | 250mg Solubility | 250mg Solvent Method | 300mg pH | 300mg Solubility | 300mg Solvent Method |
|---|---|---|---|---|---|---|---|---|---|---|---|---|---|---|---|---|---|---|---|---|---|
| LDH-IBUPROFEN | 200 mg | None | 0mg | 2.0 | 1 | (65) | | | | | | | | | | | | | | | |
| LDH-NAPROXEN | | None | 0mg | 2.3 | 0 | 52 | | | | | | | | | | | | | | | |
| LDH-KETOROLAC | | None | 0mg | 1.6 | 34 | 90 | | | | | | | | | | | | | | | |
| LDH-DICLOFENAC | | None | 0mg | 2.8 | 0 | 29 | | | | | | | | | | | | | | | |
| LDH-ATORVASTATIN | | None | 0mg | 1.7 | 1 | 58 | | | | | | | | | | | | | | | |
| IBUPROFEN FREE ACID | | None | 0mg | | 0 | 95 | | | | | | | | | | | | | | | |
| NAPROXEN FREE ACID | | None | 0mg | | 0 | 98 | | | | | | | | | | | | | | | |
| KETOROLAC FREE ACID | | None | 0mg | 1.5 | 8 | 97 | | | | | | | | | | | | | | | |
| DICLOFENAC NA SALT | | None | 0mg | 1.4 | 0 | 20 | | | | | | | | | | | | | | | |
| ATORVASTATIN CA SALT | | None | 0mg | 1.5 | 0 | 69 | | | | | | | | | | | | | | | |
| LDH-KETOROLAC | 13.56mg | Lecithin | 13.56mg | | | | 1.7 | 38 | 75 | | | | | | | | | | | | |
| LDH-IBUPROFEN | 50 mg | Lecithin | 50mg | | | | | | | 4.7 | 1 | 30 | | | | | | | | | |
| LDH-IBUPROFEN | 200 mg | Lecithin | 200mg | | | | | | | 7.1 | 4 | 55 | 7.4 | 3 | 82 | | | | | | |
| LDH-NAPROXEN | | Lecithin | | | | | | | | | | | 7.2 | 39 | 71 | | | | | | |
| LDH-KETOROLAC | | Lecithin | | | | | | | | | | | 6.3 | 4 | 34 | | | | | | |
| LDH-DICLOFENAC | | Lecithin | | | | | | | | | | | 7.0 | 1 | 20 | | | | | | |
| LDH-ATORVASTATIN | | Lecithin | | | | | 1.6 | 41 | 88 | | | | | | | | | | | | |
| LDH-NAPROXEN | 250mg | Poloxamer 407 | 250mg | | | | | | | | | | | | | 7.6 | 20 | 91 | | | |
| LDH-KETOROLAC | 3.39mg | Poloxamer 407 | 3.39mg | | | | | | | | | | | | | | | | 8.7 | 13 | 99.3 |
| LDH-KETOROLAC | 13.56mg | Poloxamer 407 | 13.56mg | | | | 1.6 | 41 | 77 | | | | | | | | | | 7.8 | 13 | 89 |
| LDH-IBUPROFEN | 50mg | Poloxamer 407 | 50mg | 1.6 | 39 | 86 | | | | | | | 8.8 | 28 | 79 | | | | | | |
| LDH-NAPROXEN | 62.5mg | Poloxamer 407 | 62.5mg | | | | | | | | | | | | | 8.2 | 20 | 92 | | | |
| LDH-IBUPROFEN | 200mg | Poloxamer 407 | 200mg | 3.2 | 21 | 64 | | | | | | | 9 | 6 | 56 | | | | | | |
| LDH-NAPROXEN | 250mg | Poloxamer 407 | 250mg | 4.5 | 3 | 56 | | | | | | | | | | 9.2 | 34 | 90 | | | |

MODIFIER SYSTEM FOR COMPOSITIONS CONTAINING LAYERED DOUBLE HYDROXIDE

CROSS-REFERENCE TO RELATED APPLICATIONS

This application is a continuation of U.S. application Ser. No. 16/343,812, filed Apr. 22, 2019, which is a United States national phase application under 35 U.S.C. § 371 of International Application No. PCT/GB2017/053237, filed Oct. 27, 2017, which claims the benefit of priority to United Kingdom Patent Application No. 1618204.0, filed Oct. 27, 2016, the contents of which are incorporated herein by reference in their entireties.

FIELD OF THE INVENTION

The present invention relates to compositions which contain i) layered double hydroxide (LDH) materials intercalated with one or more active anions (LDH-active anion materials), together with ii) a modifier system for controlling the release of the active anion from the LDH-active anion material and for controlling the solubility of the released active anion in acidic media. The present invention particularly relates to compositions in which the active anion in the LDH-active anion material is a pharmaceutically and/or a nutraceutically active anion, and to the use of such compositions in formulations suitable for pharmaceutical and/or nutraceutical applications.

BACKGROUND OF THE INVENTION

A review of layered double hydroxides (LDHs) is given in Chemistry in Britain, September 1997, pages 59 to 62, and briefly, these materials are either mixed hydroxides of monovalent and trivalent metals or mixed hydroxides of divalent and trivalent metals, having an excess of positive charge that is balanced by interlayer anions. Such materials can be represented either by:

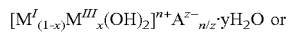

$[M^{I}_{(1-x)}M^{III}_{x}(OH)_2]^{n+}A^{z-}_{n/z}\cdot yH_2O$ or

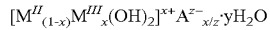

$[M^{II}_{(1-x)}M^{III}_{x}(OH)_2]^{x+}A^{z-}_{x/z}\cdot yH_2O$ where $M^{I}$, $M^{II}$ and $M^{III}$ are mono-, di- and trivalent metal cations respectively, that occupy octahedral positions in hydroxide layers; $A^{z-}$ is an interlayer charge-compensating anion; z is an integer; n=2x−1; x is less than 1; and y is ≥0.

The methods used in the manufacture of LDH materials are well documented and can include ion exchange, co-precipitation, rehydration, secondary intercalation, re-coprecipitation, and templated synthesis methods, see for example He et al., *Struct. Bond*, 2006, 119, p. 89-119. There are also different methods for preparing LDH materials intercalated with large active anions for example pharmaceutically active molecules and biomolecule, as described in EP0987328 (B1), WO2010/089691A1, CN101597474B and EP0550415 A2.

In all end-use applications involving LDH-active anion materials it is important to control release of the intercalated active anion from the layers of the LDH structure; firstly, to exert control over the onset and extent of efficacy of the active anion (especially relevant when the active anion is pharmaceutically and/or nutraceutically active), and secondly by controlling active anion release it is possible to improve the safety, toxicity, ease of use and/or ease of handling of the LDH-active anion material.

In their earlier patent application PCT/GB2013/052554, the Applicant describes a process for making improved controlled-release LDH-active anion materials which are able to retain substantially all of the active anion within the LDH matrix whilst in the absence of ion exchange conditions and/or under conditions where the pH is >4. These improved LDH-active anion materials are particularly useful in orally delivered formulations which call for the need to taste-mask an active anion that is poor-tasting, or which causes burn, irritation or some other unacceptable sensation, within the mouth, buccal cavity or larynx; the pH of the mouth is pH 6.2-7.6, and the improved LDH-active anion materials are designed to retain the active anion within the LDH structure until after swallowing. Non-standard tablet formulations such as chewable tablets, orally disintegrating tablets, orally disintegrating granules and lozenges which are sucked or chewed are easier for a patient to take than dry tablets, but since the LDH-active anion will remain in the mouth for a few minutes before with taste masking ability in order to reduce non-compliance by patients, particularly within paediatrics patient groups.

As well as controlling the release of the active anion in the mouth, it is also important to control the release and solubility of the active anion from the LDH lattice when the LDH-active anion material enters the gastrointestinal tract.

EP 1341556(B1) teaches controlling or modifying the release of a pharmaceutically active compound from a drug delivery system comprising LDH materials intercalated with pharmaceutically-active anionic compounds by incorporating a buffer into the formulation, or alternatively, by incorporating an anion-containing non-toxic compound. In use, the anion in the non-toxic compound is described as preferentially displacing the pharmaceutically-active compound from within the layers of the LDH. The non-toxic compounds preferred in this prior art contain carbonate or hydrogen carbonate anions, such as $CaCO_3$, $Ca(HCO_3)_2$, $MgCO_3$ and $Mg(HCO_3)_2$. However, the Applicant has found that these non-toxic compounds produce only a slight increase in the solubility in an acid medium of an acid insoluble active anion, such as ibuprofen, when it is displaced from within the layers of the LDH-active anion material. At this low solubility level it is highly unlikely that it will be possible to achieve a pharmacokinetic profile comparable with that obtained for the Ibuprofen free acid. Furthermore, contrary to the teachings in EP1341556(B1), the Applicant has evidence to indicate that metal carbonates do not promote much more active anion to be released from within the layers of the LDH matrix, than the amount which is released when a metal carbonate is not present.

As discussed by B. S. Sekhon in J. Pharmaceutical Technology Research and Management, vol. 1 2013, 11-36: "Surfactants: Pharmaceutical and Medicinal Aspects", surfactants are known to be components of many pharmaceutical products, for example i) to solubilise hydrophobic drugs in aqueous media, ii) as components of emulsions, iii) as surfactant self-assembly vehicles for oral and transdermal drug delivery, iv) as plasticisers in semisolid delivery systems and v) as agents to improve drug absorption and penetration. Non-ionic surfactants such as ethers of fatty alcohols are most commonly used in pharmaceuticals and serve as emulsifiers, wetting agents, solubilisers and dispersants. Further, D. Ramya Devi et al have compiled a review of the different attributes of poloxamer and its application in drug delivery in J. Pharm. Sci. & Res. Vol. 5(8), 2013, 159-165: "Poloxamer: A Novel Functional Molecule For Drug Delivery and Gene Therapy".

However, a research paper by P. Dewland et al, BMC Clinical Pharmacology 2009, 9:19: "Bioavailability of ibuprofen following oral administration of standard ibuprofen, sodium ibuprofen or ibuprofen acid incorporating poloxamer in healthy volunteers" concludes that poloxamer 407 surfactant is ineffective to enhance the dissolution and bioavailability of poorly water soluble drugs, including ibuprofen.

Moreover, although several other studies report an increase in the solubility of ibuprofen in acidic media as a result of the presence of a poloxamer 407 or 188 (non-ionic surfactants), this is disclosed as only being possible when the two ingredients are in the form of a binary solid dispersion, for example, R. P Dugar et al "Preparation and Characterization of ibuprofen-Poloxamer 407" in AAPS PharmSciTech 2016 Jan. 27 [Epub ahead of print], and M. Newa et al "Preparation, characterization and in vivo evaluation of ibuprofen binary solid dispersions with poloxamer 188", International Journal of Pharmaceutics, Volume 343, Issues 1-2, 1 Oct. 2007, Pages 228-237. Further, the enhanced ibuprofen solubility is reported in these papers to be due to the formation of eutectics between the ibuprofen and the poloxamer, rather than due to the presence of the surfactant per se. The loss of ibuprofen crystallinity in the fused ibuprofen/poloxamer mixture was confirmed by XRPD, and is disclosed to be the principle cause of the increased solubility.

Meanwhile, Hoo-Kyun Chi and Sung-Hyun Park report in the International Journal of Pharmaceutics 321 (2006) 35-41: "The effects of surfactants on the dissolution profiles of poorly water-soluble acidic drugs", that the dissolution of acidic drugs such as mefenamic acid, nimesulfide and ibuprofen is substantially enhanced in a medium containing cetyltrimethylammonium bromide (CTAB), a cationic surfactant, as compared against sodium lauryl sulfate (SLS), an anionic surfactant, or polysorbate 80, a non-ionic surfactant.

Notwithstanding the prior art discussed above, there is a need 1) to control the amount of active anion which is released from between the layers of LDH in an LDH-active anion material, and also 2) to control the solubility of the released active anion in acidic media, particularly in the case of poorly water soluble active anions such as ibuprofen. Controlling release to increase the amount of active anion released and increasing its solubility in the stomach may lead to faster and increased absorption. Conversely, controlling release to reduce the amount released in the stomach may provide for slower absorption.

STATEMENT OF THE INVENTION

The aim of the present invention is to provide compositions which contain LDH-active anion materials and which enable the controlled release of the active anion from within the LDH layers, when in an acidic media designed to represent the conditions found in a fasted human stomach. Advantageously, the active anion is a pharmaceutically and/or nutraceutically active anion.

It is desirable that the compositions of the present invention control the release of the active anion by effecting either an increased or a decreased amount of active anion to be released from within the LDH layers of an LDH-active anion material, relative to the amount released by the LDH-active anion alone, in an acidic media.

Another key goal of the present invention is to provide compositions which contain LDH-active anion materials and which enable the controlled solubilisation of the active anion in acidic media.

Thus, a further aim is to provide compositions which contain LDH-active anion materials and from which release of the active anion is controlled so as to either exhibit a fast and increased absorption of the active anion in the gastrointestinal (GI) tract, or alternatively when a reduced amount of active anion is released, to exhibit a slower absorption in the GI tract.

The present invention, therefore, provides a composition comprising: i) one or more LDH-active anion materials comprising an LDH matrix intercalated with one or more active anions, and ii) a modifier system comprising a) one or more surfactants, in combination with b) one or more pharmaceutically acceptable salts having the generic formula MA, where M comprises or, in the alternative consists essentially of, one or more positively charged ions cations) and A comprises, or in the alternative consists essentially of, one or more negatively charged counter ions (anions).

As demonstrated in the specific examples below, the present invention provides a composition which contains a modifier system which is capable of 1) controlling the total amount of active anion released from the LDH matrix under acidic conditions designed to represent the conditions found in a fasted human stomach, compared against the amount which is released when the modifier system is absent or when a surfactant is used alone and 2) controlling the amount of active anion which is dissolved in the acidic medium, compared against the amount which is dissolved when a surfactant is used alone or when a metal salt is used alone or when the modifier system is absent. "Controlling the amount of active anion which is dissolved in the acidic medium", shall be interpreted to mean that a greater amount or a reduced amount of active anion may be dissolved in the acidic medium by the use of the modifier system of the present invention.

In one embodiment, the present invention provides a composition which contains a modifier system which is capable of promoting a significant increase in the amount of active anion which is released and dissolved in acidic media that is designed to represent the conditions found in a fasted human stomach, when compared against the amount of active anion which is released and dissolved under comparable conditions in the presence of either a surfactant alone or when in the presence of a metal salt alone or when the modifier system is absent.

In another embodiment, the present invention provides a composition which contains a modifier system which is capable of promoting a significant reduction in the amount of active anion which is released and, at the same time, controlling the solubility of the active anion which is released in acidic media designed to represent the conditions found in a fasted human, compared against the amount of active anion which is released and dissolved under comparable conditions using a surfactant alone or a metal salt when used alone or when the modifier system is absent.

The Applicant has unexpectedly found that the combination of one or more surfactants and one or more compounds having the generic formula MA used in the modifier system of the present invention, shows synergistic activity towards the release and solubility of an active anion in acidic media. Further, that this synergistic activity allows for the amount of surfactant to be reduced whilst maintaining the desired active anion release and solubility in acidic media. A reduction in the amount of surfactant is particularly advantageous for pharmaceutical and nutraceutical formulations where high levels of surfactant would be expected to be unpalatable due to their soapy taste, and depending on the surfactant used, could have an undesirable safety profile. Not only this, processing and formulation difficulties are also expected with high surfactant levels, for example it is likely to be difficult to ensure that the ingredients are uniformly blended, and there may be an issue with forming tablets with the desired hardness.

The modifier system comprises any suitable surfactant, which is preferably a pharmaceutically acceptable surfactant. Ideally the modifier system comprises one or more surfactants selected from:

1) anionic surfactants such as carboxylates: alkyl carboxylates (e.g. fatty acid salts), carboxylate fluorosurfactants; sulfates: alkyl sulfates (e.g. sodium lauryl sulfate), alkyl ether sulfates (e.g. sodium laureth sulfate); sulfonates: docusates (e.g. dioctyl sodium sulfosuccinate), alkyl benzene sulfonates; phosphate esters: alkyl aryl ether phosphates and alkyl ether phosphates.
2) Zwitterionic (amphoteric) surfactants, which can be anionic, cationic or non-ionic depending on the pH of the solution they are in. Examples include: $RN^+H_2CH_2COO^-$, $RN^+(CH_3)_2CH_2CH_2SO_3^-$, phospholipids such as phosphatidylcholine (lecithin).
3) Cationic surfactants which bear a positive charge for example $RN^+H_3Cl^-$, $RN^+(CH_3)_3Cl^-$, diotadecyldimethylammonium chloride, cetyl pyridinium chloride or benzalkonium chloride.
4) Non-ionic surfactants which are uncharged. Examples include: polyol esters (e.g. glycol, glycerol esters, sorbitan and sorbitan derivatives such as fatty acid esters of sorbitan (Spans) and their ethoxylated derivatives (Tweens)), polyoxyethylene esters and poloxamers.

The Applicant has found that anionic, zwitterionic and non-ionic surfactants are particularly useful in the modifier system used in the composition of the present invention.

As used herein, the term "pharmaceutically acceptable" in relation to any of the ingredients or excipients included in the composition of the present invention is to be interpreted to mean that the ingredient or excipient is permitted, e.g. by national regulatory agency approval, to be used in pharmaceutical and/or nutraceutical formulations and/or any other formulation for human or animal use and/or consumption.

Contrary to what would be expected from the known interactions between a surfactant and an active anion, as described above in relation to various prior art documents, the surfactants in the modifier system used in the present invention do not merely act to increase the solubility of the active anion once it has been released. Indeed, as the results presented below in the specific examples demonstrate, although the presence and chemical nature of a surfactant has a strong influence over the amount of active anion which is released, not all surfactants promote an increase in the solubility of the active anion.

Preferred surfactants to be used in the modifier system of the present invention, therefore, are those which intercalate and/or interact with the LDH portion of the LDH-active anion material, either in addition to, or in the alternative to, controlling the solubility of the active anion following its release from the LDH matrix. Anionic surfactants such as sodium lauryl sulfate work very effectively and are believed to interact with the cationic layers of the LDH, however, the Applicant has unexpectedly found that poloxamers, which are non-ionic surfactants and lecithin, which is a zwitterionic surfactant, also interact in some way with the LDH to cause the active anion to be released from the LDH matrix, thus making these surfactants surprisingly highly effective in the modifier system used in the compositions of the present invention.

The Applicant has also unexpectedly found that the choice of surfactant will increase or decrease the amount of active anion being released from the LDH matrix, depending on the specific active anion being released. For example as described in the specific examples below, the Applicant has conducted tests to determine the amount of active anion released from the LDH matrix after 15 minutes (to replicate normal in vivo activity where material is retained in the stomach for about 15 minutes). In the case of some LDH-active anion materials (e.g. LDH-ibuprofen, LDH-naproxen, LDH-diclofenac and LDH-ketorolac) a modifier system comprising at least one surfactant selected from zwitterionic, anionic and non-ionic surfactants is found to lead to an increase in the amount of active anion released, whereas use of a cationic surfactant is found to reduce the amount of active anion released; in both cases compared against the amount of active anion released in the absence of the modifier system. By contrast, in the case of other LDH-active anion materials (e.g. LDH-atorvastatin), a zwitterionic surfactant (e.g. lecithin) is observed to decrease the amount of active anion released.

In pharmaceutical applications, irritant and cancer concerns arise in respect of certain surfactants, for example sodium lauryl sulfate, therefore poloxamer and lecithin are especially preferred in compositions which are to be used in pharmaceutical and/or nutraceutical formulations. Further, for taste masked formulations, poloxamer is preferred since high levels of lecithin have an unpleasant odour. Poloxamer 407 is found to be particularly useful.

The compounds of the generic formula MA are preferably pharmaceutically acceptable salts which further preferably have a solubility of at least 0.002 g/ml, and particularly preferably a solubility of at least 0.006 g/ml, in the simulated stomach acid media (0.2% sodium chloride in 50 ml 0.05M hydrochloric acid). Ideally the compounds MA comprise one or more cations, M, which are preferably one or more metal cations. These may be selected from mono-, di-, or tri-valent metals, and preferably selected from alkali metals, alkaline earth metals and transition metals. Highly preferred one or more cationic metals M are selected from iron, magnesium, aluminium, calcium, sodium, lithium, potassium, rubidium, caesium, barium, strontium, beryllium, manganese, cobalt, nickel, copper, silver, zinc, cadmium, titanium, lead, lanthanum and cerium; and one or more metals selected from calcium, magnesium, aluminium, lithium, sodium, potassium, iron and zinc are particularly preferred, and sodium, lithium, magnesium, calcium aluminium are the most preferred. In another embodiment the one or more cations, M, may comprise non-metallic cations for example ammonium, diethylamine or similar cations.

The compounds of the generic formula MA also comprise one or more anionic counter ions, A. Any suitable anionic counter ion may be used and preferably this is a pharmaceutically acceptable anionic counter ion. Suitable one or more anionic counter ions are selected from carbonate, hydrogen carbonate, sulfate, hydroxide, oxide, chloride, bromide, fluoride, nitrate, dihydrogen phosphate, hydrogen phosphate, phosphate, acetate, maleate, citrate, mesylate, tartrate, gluconate, formate, malate, oxylate, succinate, tosylate, fumarate, pamoate, furoate, propionate, saccharate and thiocyanate anions. Particularly useful compounds of the generic formula MA contain at least one carbonate and/or a hydrogen carbonate anion, and are preferably selected from magnesium carbonate, magnesium hydrogen carbonate, calcium carbonate, calcium hydrogen carbonate, sodium carbonate, sodium hydrogen carbonate, lithium carbonate and lithium hydrogen carbonate. Sodium carbonate and sodium hydrogen carbonate are especially preferred.

In the one or more LDH-active anion materials, the amount of LDH is present in an amount greater than 40% by weight of the LDH-active anion material. An amount of LDH of 50% by weight of the LDH-active anion material is ideal in the case of LDH-ibuprofen for example, but an amount of LDH greater than 60% by weight of the LDH-active anion material may also be used, as can an amount of LDH of 70% by weight of the LDH-active anion material, for example when the active anion material is atorvastatin.

As used herein, the term "active anion" includes any compound or molecule that is anionic (i.e. a molecule with a negative charge) or from which an anion is generated, for example by dissolving the free acid or salt form of a compound/molecule in aqueous solution. An anionic compound/molecule is interpreted to be "active" in the sense that it produces a chemical, physical, physiological, nutraceutical or pharmaceutical effect which is preferably recognised in an animal or human body. Suitable active anions may be simple anions or they may be larger and/or have more complex structures. Examples of compounds which contain an active anion may include additives used in medicaments, food supplements and vitamin supplements nutraceuticals and pharmaceuticals.

Preferred compounds which contain an active anion are those which produce a pharmaceutical effect, and these pharmaceutical compounds may include the classes of NSAIDS, gaba-analogues, antibiotics, statins, angiotensin-converting enzyme (ACE) inhibitors, antihistamines, dopamine precursors, anti-microbials, psychostimulants, prostaglandins, anti-depressants, anti-convulsants, coagulants, anti-cancer agents, immunosuppressants and laxatives. Preferred pharmaceutical compounds include: ibuprofen, naproxen, ketorolac, diclofenac, indomethacin and atorvastatin, all in salt (e.g. sodium and calcium) and/or free acid form.

It is believed that the compositions of the present invention will be particularly advantageous in relation to acidic pharmaceutical compounds and/or those which are largely insoluble in acid media, for example ibuprofen.

The modifier systems used in the compositions of the present invention are able to control the amount of active anion released to be in the range 20% to 90% of the total amount of active anion present in the LDH-active anion material. As demonstrated in the specific examples below, the amount of ibuprofen released from an LDH-ibuprofen material is 65% of the total available in the absence of a modifier system and 41% release in the presence of 300 mg sodium carbonate without a surfactant (400 mg LDH-ibuprofen equivalent to a 200 mg dose of ibuprofen) in acidic media. Also as demonstrated below, it is possible to increase the solubility of the active anion (ibuprofen) which is released so that 57% is dissolved in acidic media (compared against 0.9% of the ibuprofen being dissolved in the absence of a modifier system and 25% of the ibuprofen being dissolved in the presence of 300 mg sodium carbonate without a surfactant (400 mg LDH-ibuprofen equivalent to a 200 mg dose of ibuprofen).

Surprisingly, the amount of the LDH matrix relative to the amount of the one or more compounds comprising the generic formula MA, as defined above, is found to be highly influential in giving the flexibility in the controlled release of the active anion from the LDH layers and also in increasing the solubility of the released active anion in acidic media, provided an amount of surfactant is also present. Preferably, weight ratio of the LDH matrix:the one or more compounds comprising the generic formula MA as defined above:the one or more surfactants, of 2:0.1 to 4:0.1 to 4.

Specifically, when the modifier system contains an amount of a compound of generic formula MA which is below a certain range, there is a reduction in the amount of active anion that is released from the LDH-active anion material as compared against the amount released when no compound of the generic formula MA is present. Thus, in a modifier system which is designed to decrease the amount of active anion released from the LDH matrix (compared against the amount which is released in the absence of the one or more compounds of generic formula MA i.e. to decrease the active anion release to less than 40%), the preferred weight ratio of LDH matrix:the one or more compounds of the generic formula MA:surfactant is 2:0.1 to 1:0.1 to 4.

On the other hand, where the modifier system is designed to increase the amount of active anion released from the LDH matrix (compared against the amount which is released when the one or more surfactant compounds are present in the absence of the one or more compounds of the generic formula MA), the preferred weight ratio of LDH matrix:one or more compounds comprising the generic formula MA:surfactant is 2:>1 to 4:0.1 to 4, and further preferably 1:1:0.25 to 1.

An especially preferred composition of the present invention comprises a modifier system which comprises 1 part by weight of LDH matrix, at least 0.5 parts by weight of one or more compounds of the generic formula MA and 1 part by weight of surfactant. An example of such a composition is: 400 mg LDH-ibuprofen (contains 200 mg LDH), at least 100 mg sodium carbonate and 200 mg of one or more surfactants selected from sodium lauryl sulfate, lecithin and poloxamer, i.e. the ingredients (LDH:MA:surfactant) in a ratio of 1:0.5:1. A highly preferred composition comprises 400 mg LDH-ibuprofen (contains 200 mg LDH), 200 mg sodium carbonate and 200 mg of lecithin i.e. the ingredients (LDH:sodium carbonate:lecithin) in a ratio of 1:1:1.

Advantageously, it has also been found that the amount of the one or more surfactants can be decreased without compromising the increased amount of active anion which is released or affecting the amount of released active anion which is solubilised in acidic media. This can be achieved by adding more of the one or more compounds of the generic formula MA; for example a weight ratio of the LDH-active anion matrix:one or more compounds of the generic formula MA:the one or more surfactants, for such a scenario can be 2:>1:0.5 to 2.

In a further embodiment the present invention provides a composition which comprises a modifier system which comprises a) a mixture of two or more surfactants, as defined above, and b) a mixture of one or more compounds of the generic formula MA, as defined above.

In an alternative embodiment the present invention provides a composition which comprises a modifier system which comprises a) a mixture of one or more surfactants, as defined above, and b) a mixture of two or more compounds of the generic formula MA as defined above.

In yet another embodiment, the present invention provides a method for 1) controlling the total amount of active anion released from the LDH matrix under acidic conditions designed to represent the conditions found in a fasted human stomach, and 2) controlling amount of released active anion which is dissolved in the acidic medium, the method comprising the step of forming a composition comprising: i) one or more LDH-active anion materials comprising an LDH matrix intercalated with one or more active anions, and ii) a modifier system comprising a) one or more surfactants, in combination with b) one or more compounds having the generic formula MA, preferably pharmaceutically acceptable salts, where M is a cation, preferably metal cation and A is an anionic counter ion, wherein the amount of released one or more active anions which is dissolved in the acidic medium is controlled (preferably increased) relative to both the amount which is dissolved when the one or more surfactants is used in the absence of the one or more compounds having the general formula MA and the amount which is dissolved when the one or more compounds having the general formula MA is used in the absence of the one or more surfactants.

Any suitable method may be used to determine the % release of the active anion and also the % solubility of the released active anion in an acid medium. In one convenient method described below, % release and % solubility were both determined after 15 minutes, although a longer or a shorter time may be used if desired, 15 minutes was chosen because this is the approximate time for gastric emptying in a fasted stomach. 0.05M Hydrochloric acid was chosen as the acid medium as this is a reasonable approximation of the acidity found in the human stomach, however, any other suitable medium may be used instead.

The compositions of the present invention are useful in a wide range of storage, carrier and delivery system applications for pharmaceutical and nutraceutical applications, especially where it is required to control the release of the active anion. The compositions of the present invention advantageously allow for control of the release under the acid conditions of the fasted human stomach, of the active anion from LDH-active anion materials which are highly resistant to leaching, for example when substantially all of the active anion is retained within the LDH matrix whilst the absence of ion exchange conditions and/or under conditions of above pH 4.

Therefore the present invention provides for the use of a composition as a carrier, a storage system and/or in a delivery system, said composition comprising i) one or more LDH-active anion materials, and ii) a modifier system comprising a) one or more surfactants, and b) one or more compounds of the generic formula MA, wherein the one or more surfactants and the one or more compounds of the generic formula MA are defined above.

The present invention also provides for the use of the composition of the present invention in oral pharmaceutical and/or nutraceutical applications, and in a further aspect, the compositions of the present invention are for use in the preparation of pharmaceutical and/or nutraceutical formulations.

Therefore, the present invention provides a formulation comprising a composition containing i) one or more LDH-active anion materials, and ii) a modifier system comprising a) one or more surfactants, in combination with b) one or more compounds of the generic formula MA, as defined above, selected from dry granules, tablets, caplets, orally disintegrating tablets, orally disintegrating granules, lozenges, films, capsules, powders, effervescent formulations and buccal and sub-lingual formats.

Advantageously the formulation according to the present invention comprises a composition which allows for the control of release of the active anion from the LDH-active anion material contained therein.

BRIEF DESCRIPTION OF THE DRAWINGS

The present invention will now be described with reference to the following figures in which:

FIG. 28 is a table of the % solubility and % release results obtained in Experiment 4; and FIG. 29 is a table of the % solubility and % release results obtained in Experiment 5.

DETAILED DESCRIPTION

Experiment 1—Comparing the In Vitro and In Vivo Rate of Release of 400 mg Ibuprofen from LDH-Ibuprofen Tablet Against the Rate of Release of Ibuprofen from Brufen®

The in vitro dissolution testing of the rate of release of ibuprofen from a tablet formulation of LDH-ibuprofen (400 mg ibuprofen) compared against rate of release of ibuprofen from Brufen®, a commercially available tablet formulation containing 400 mg ibuprofen, showed comparable release of >95% after 5 minutes.

Figure 1:
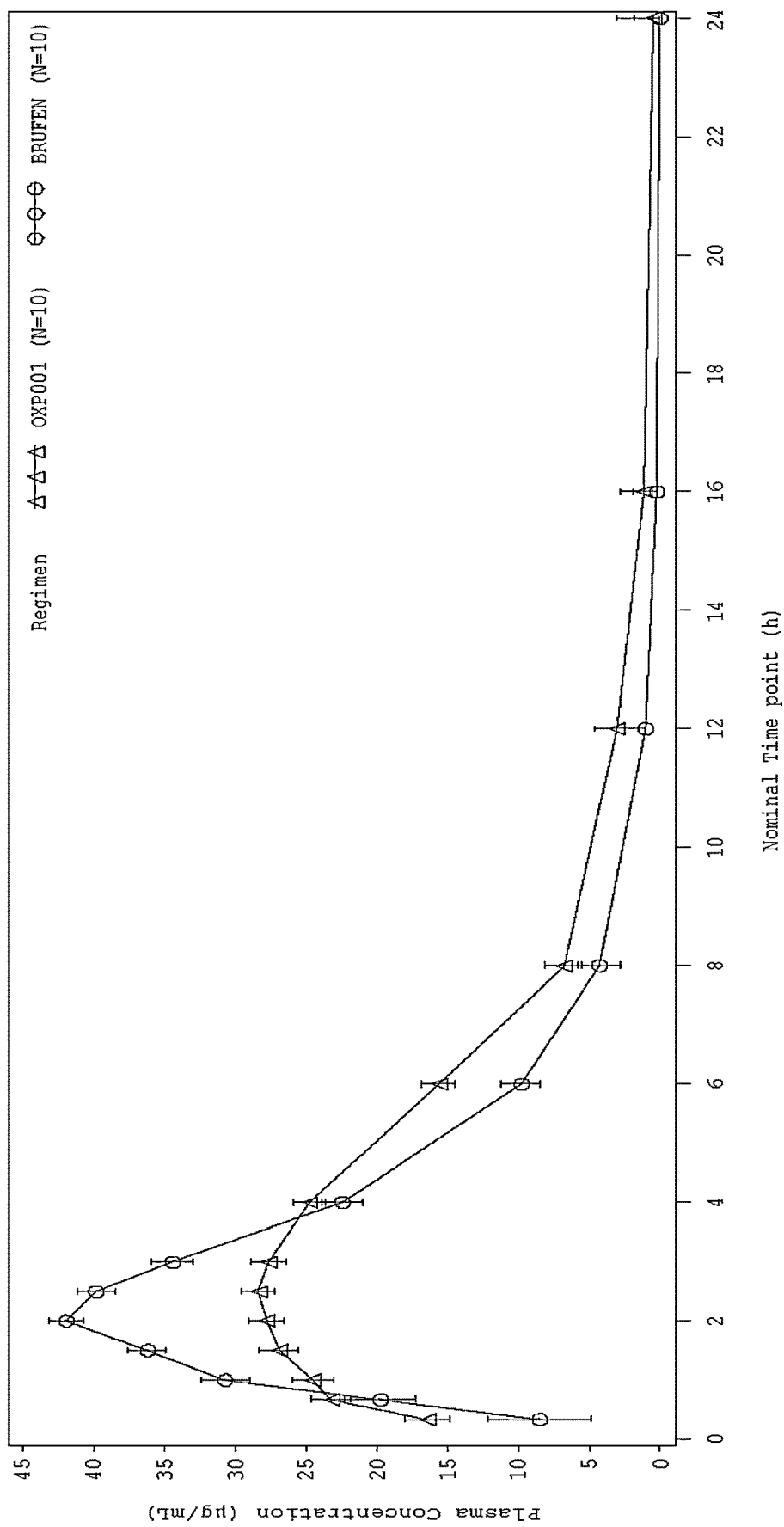
FIG. 1 is a graph of geometric mean concentration against time to compare the Brufen® single dose PK with that obtained for LDH-ibuprofen.
Figure 2:
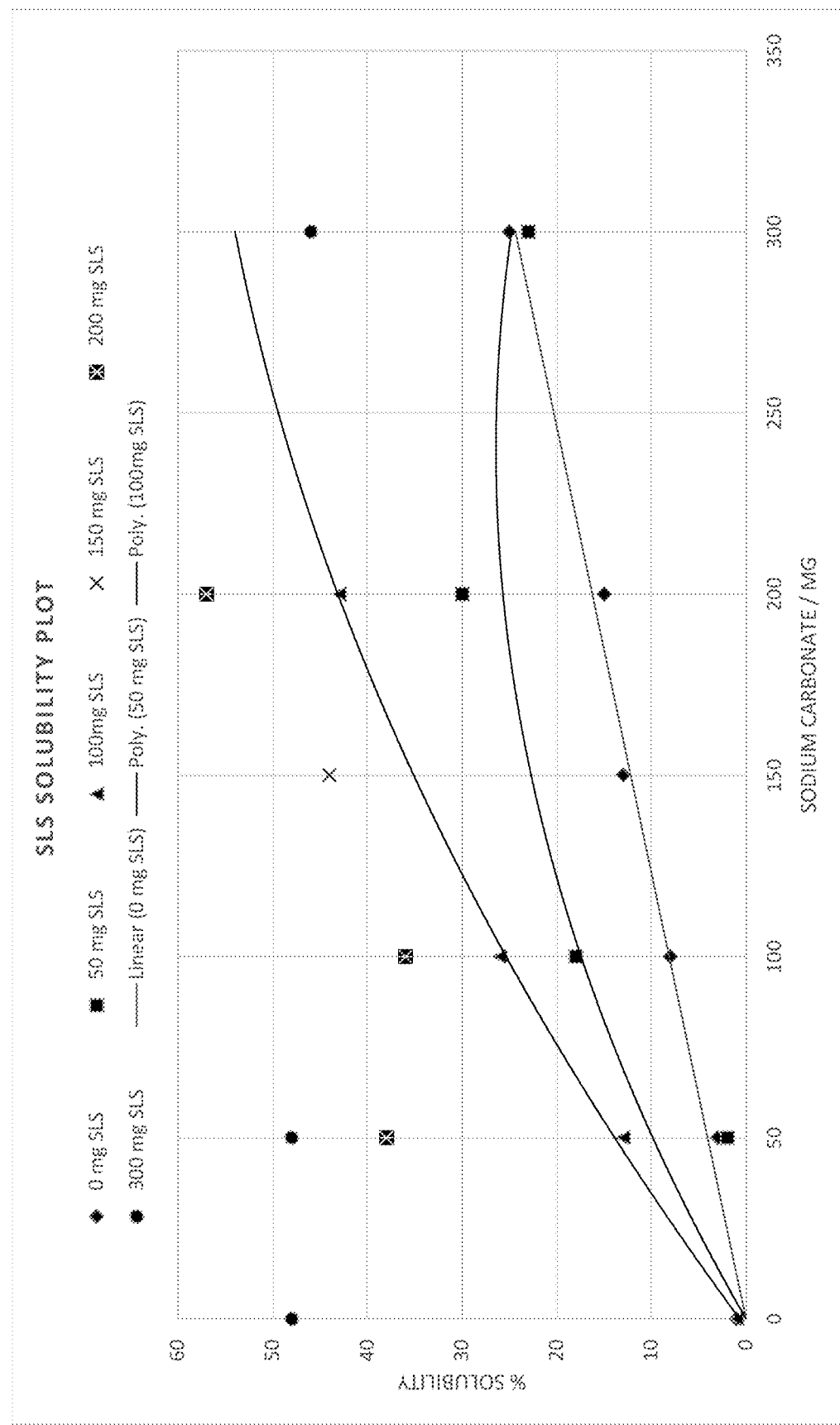
FIG. 2 is a graph of % solubility v the amount of sodium carbonate, for sodium lauryl sulfate (SLS) surfactant.
Figure 3:
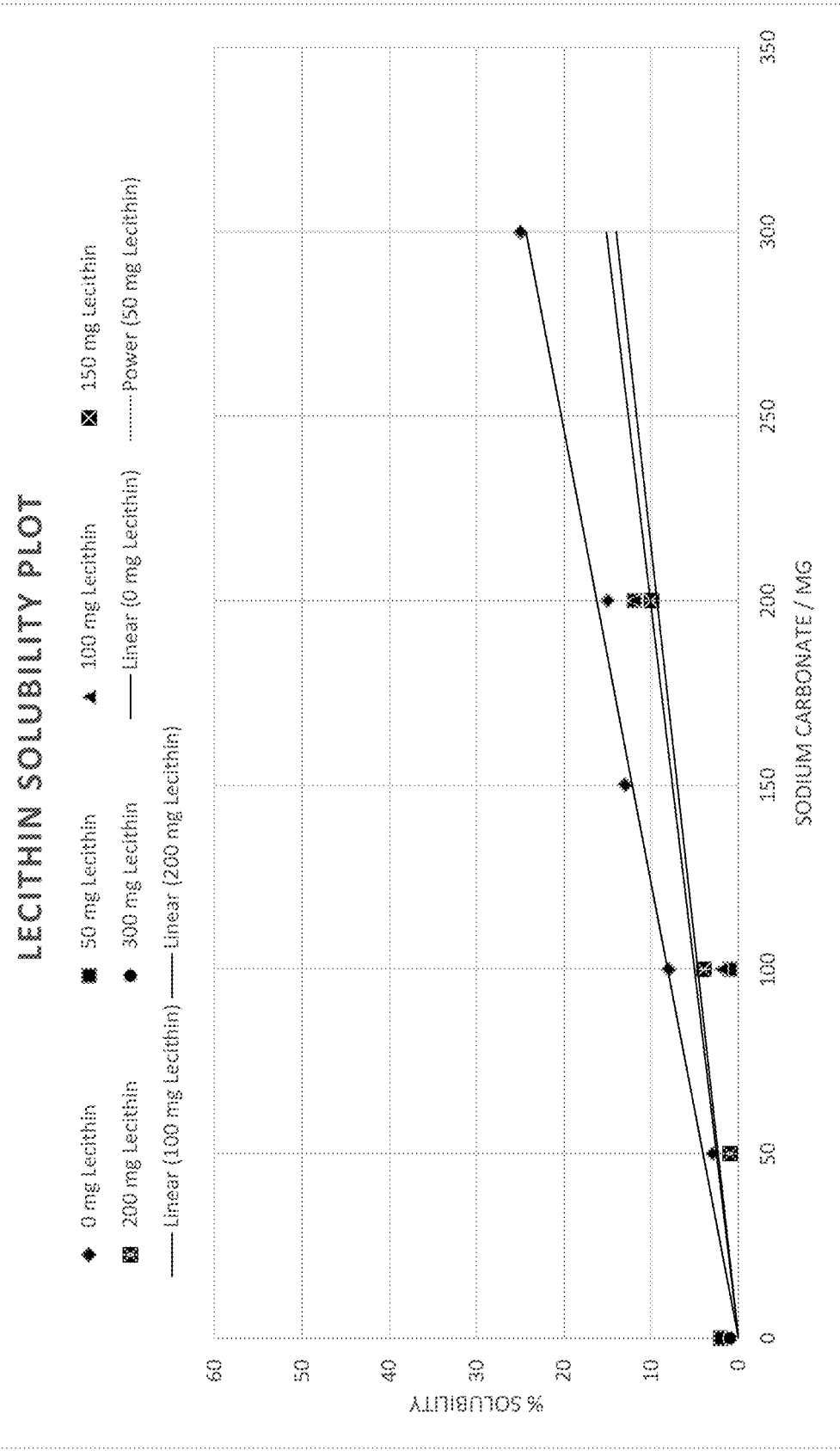
FIG. 3 is a graph of % solubility v the amount of sodium carbonate, for lecithin surfactant.
Figure 4:
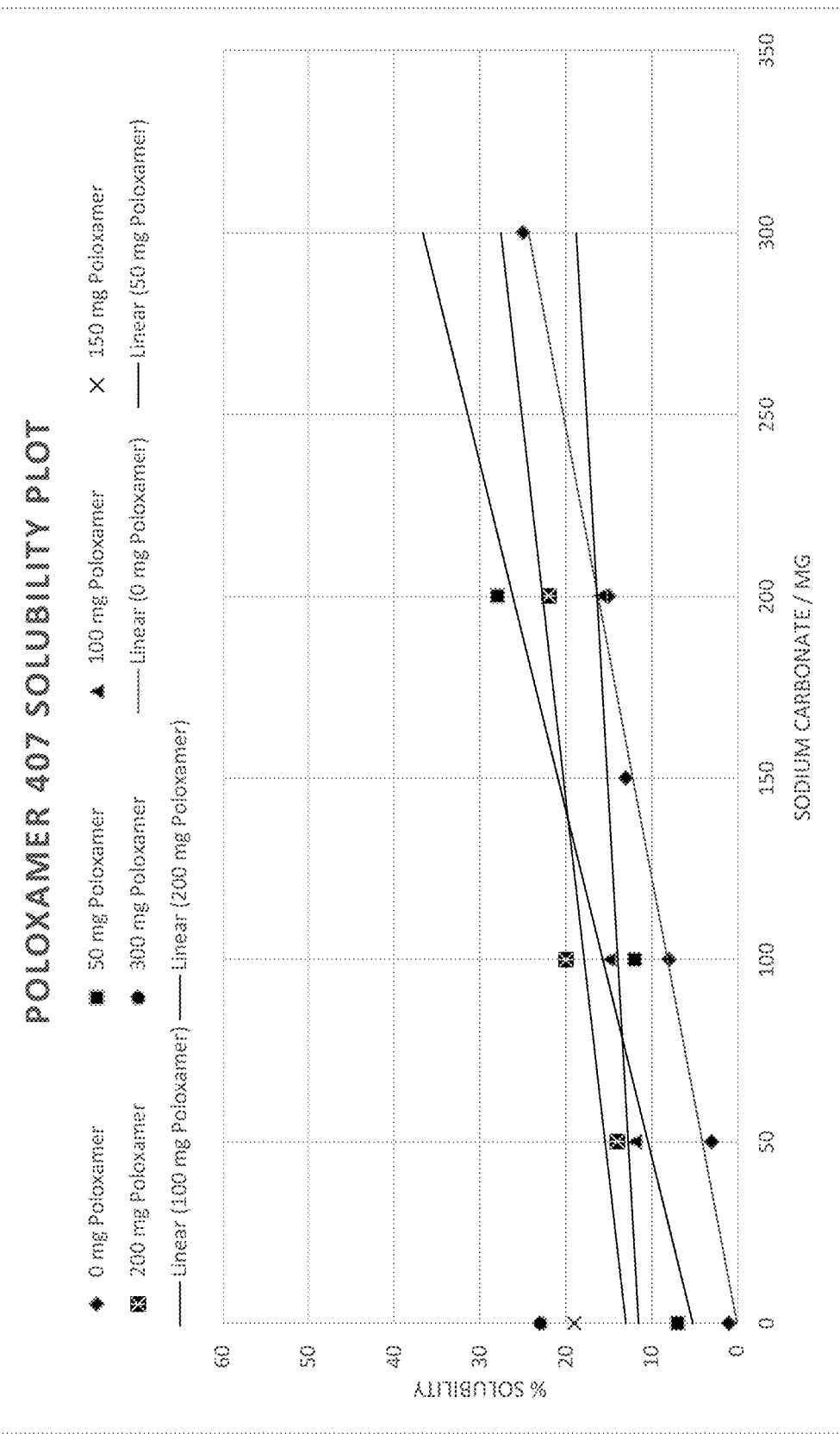
FIG. 4 is a graph of % solubility v the amount of sodium carbonate, for poloxamer 407 surfactant.
Figure 5:
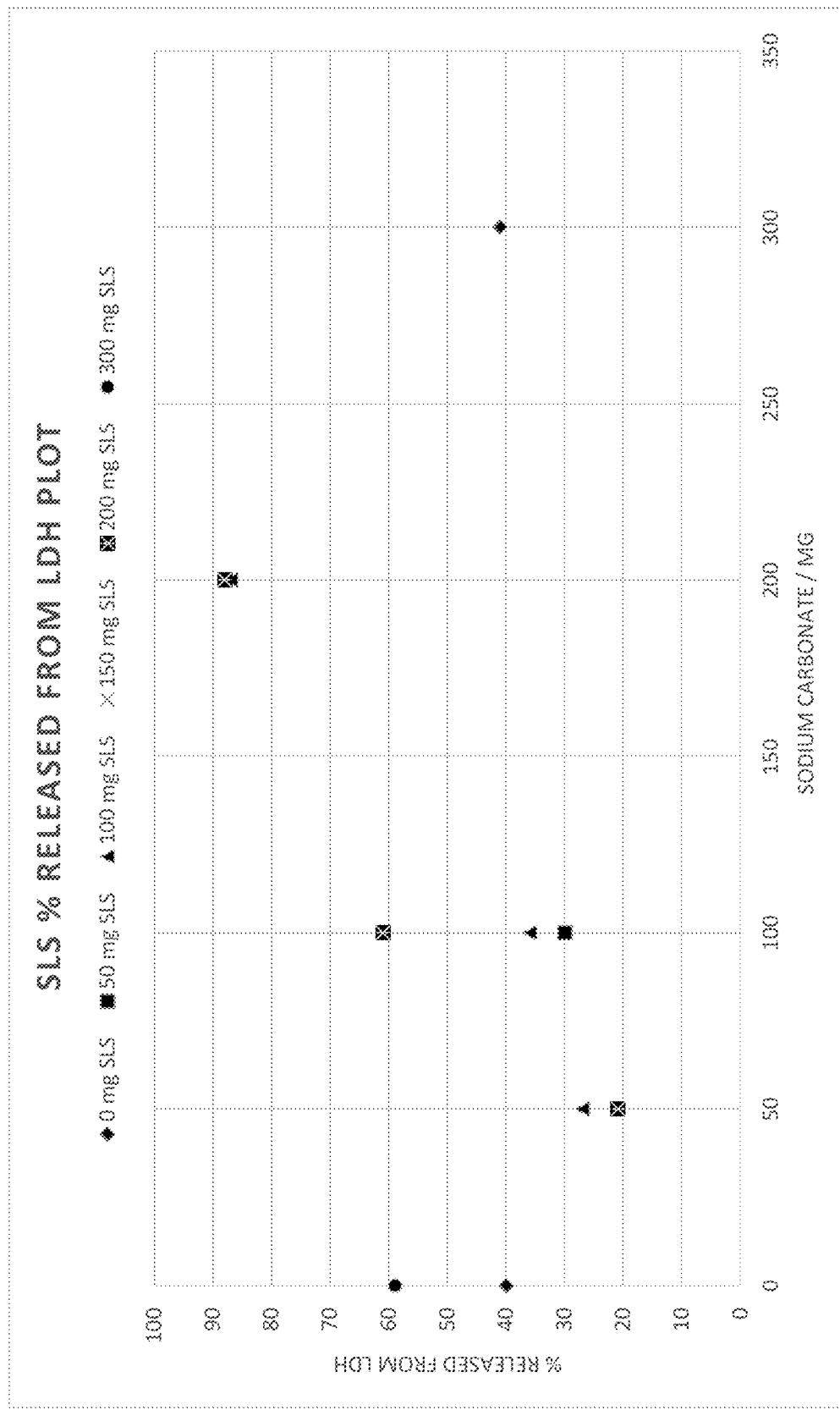
FIG. 5 is a graph of % active anion released v the amount of sodium carbonate, for sodium lauryl sulfate (SLS) surfactant.
Figure 6:
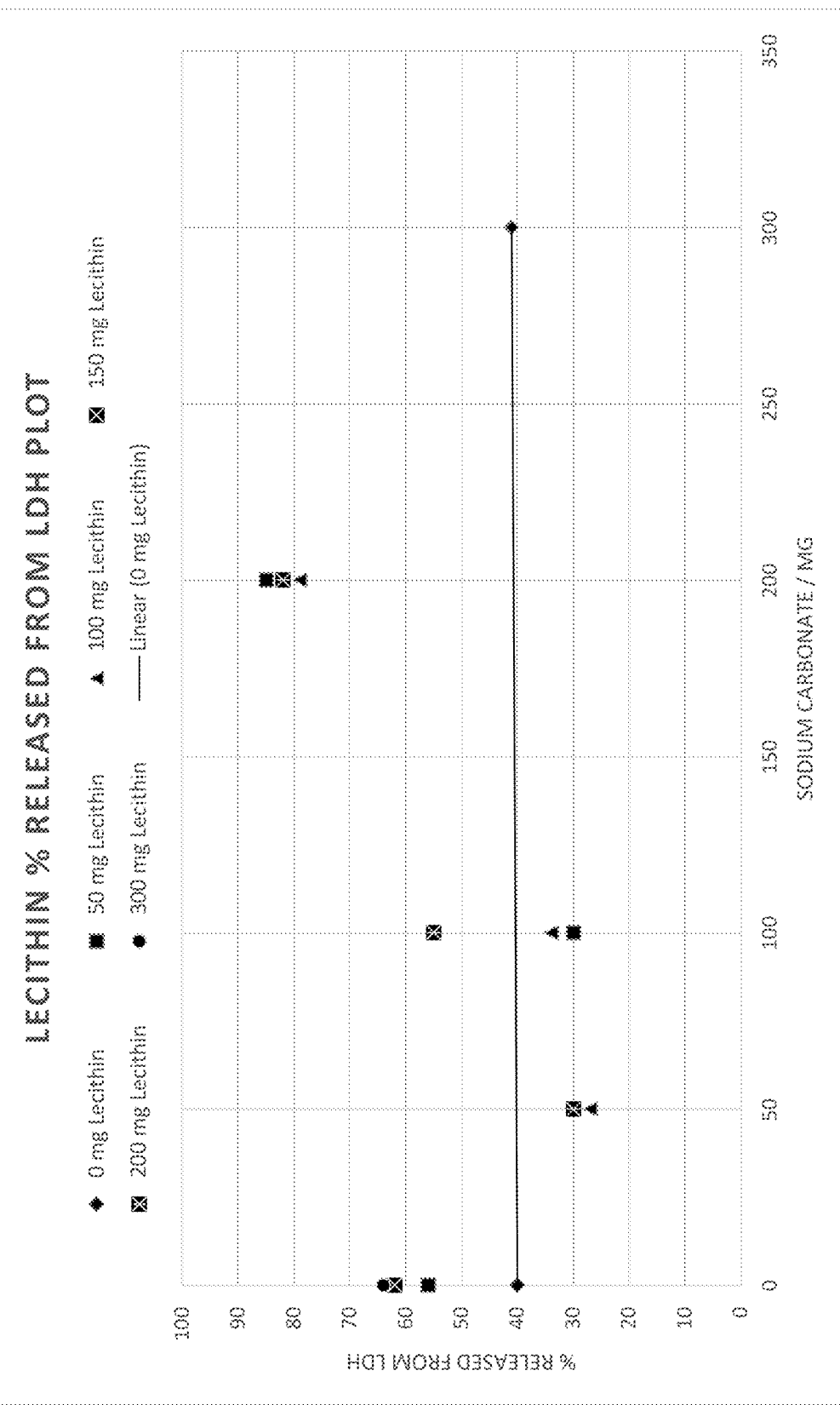
FIG. 6 is a graph of % active anion released v the amount of sodium carbonate, for lecithin surfactant.
Figure 7:
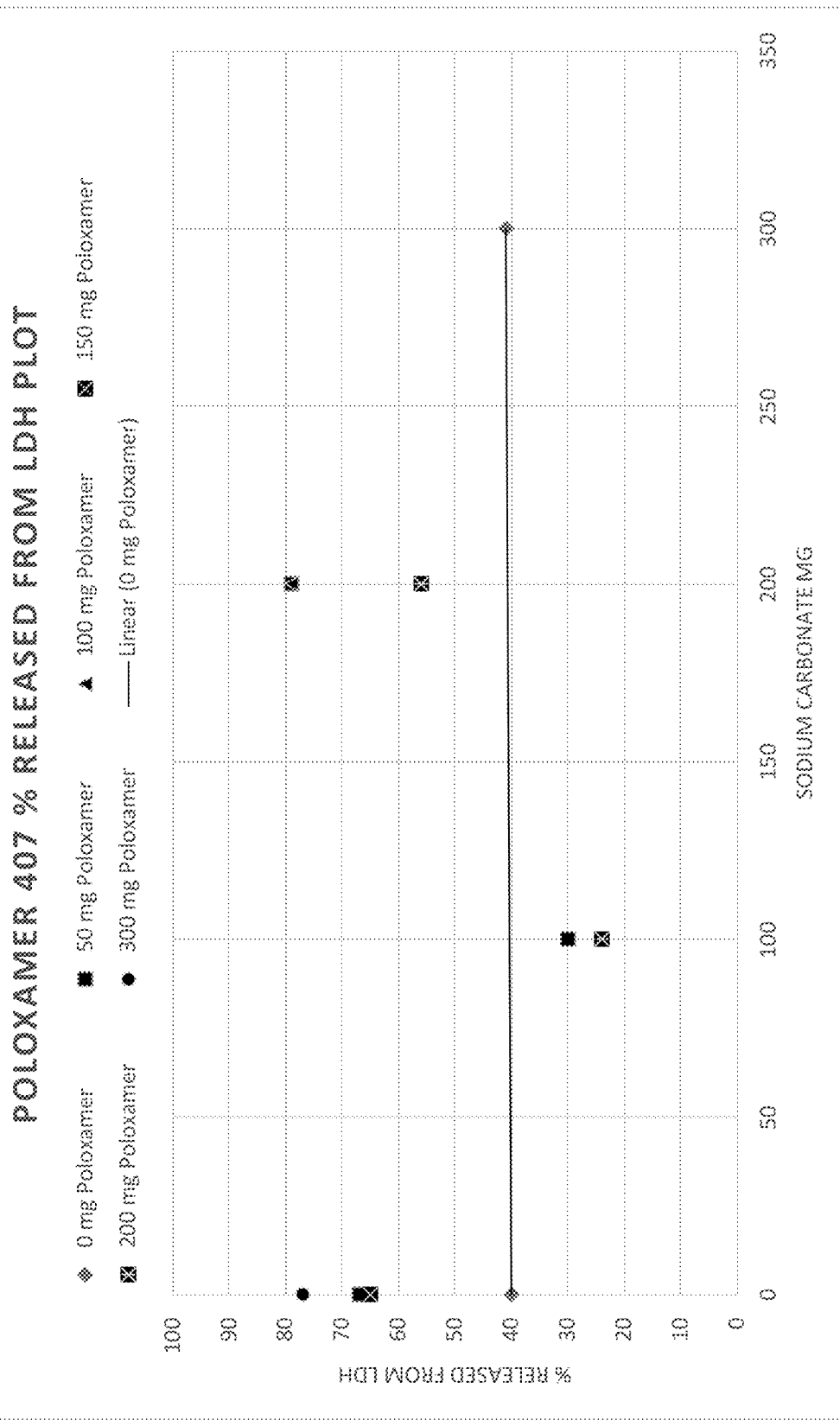
FIG. 7 is a graph of % active anion released v the amount of sodium carbonate, for poloxamer 407.
Figure 8:
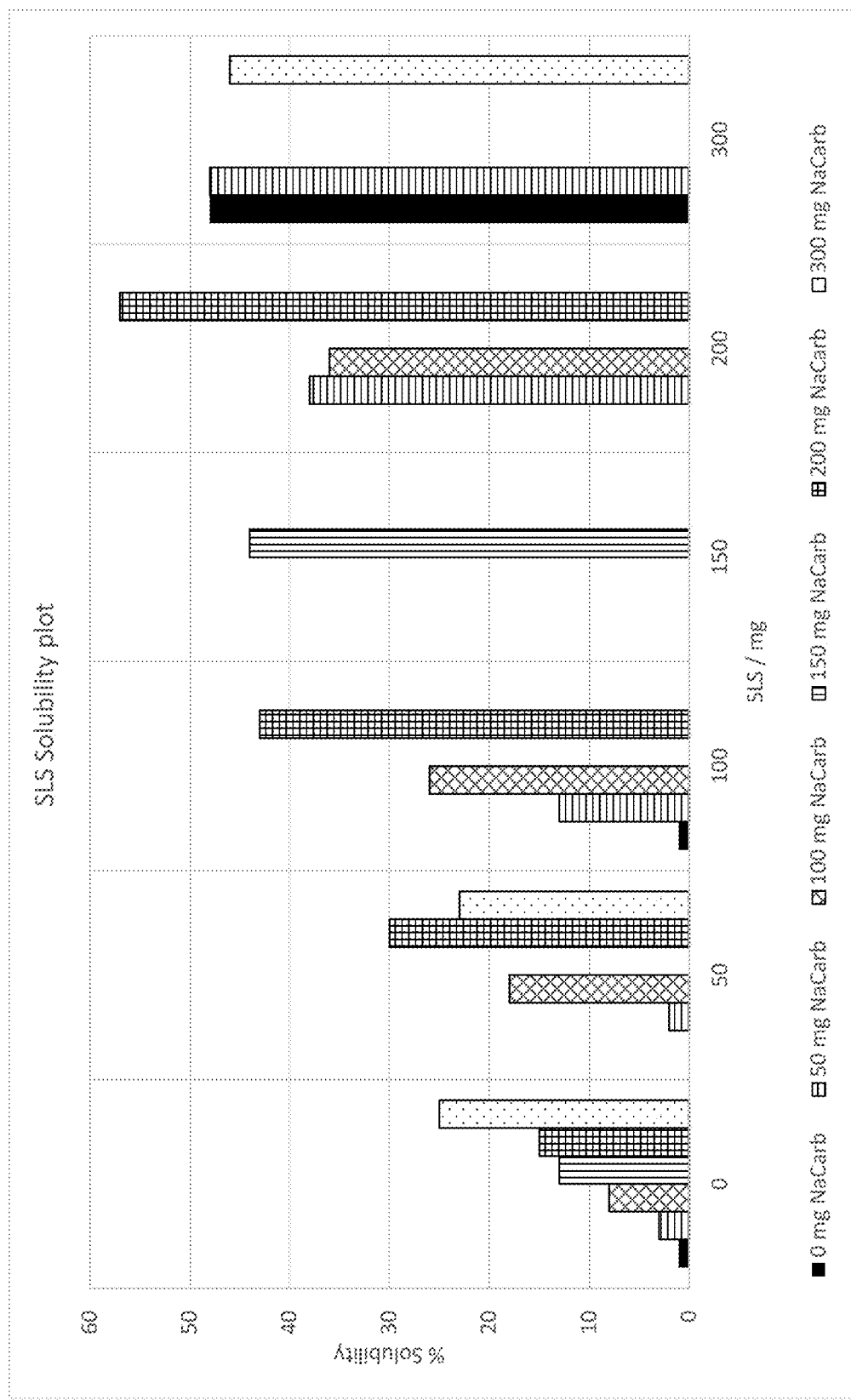
FIG. 8 is a bar graph showing % solubility v amount of sodium lauryl sulfate (SLS) surfactant.
Figure 9:
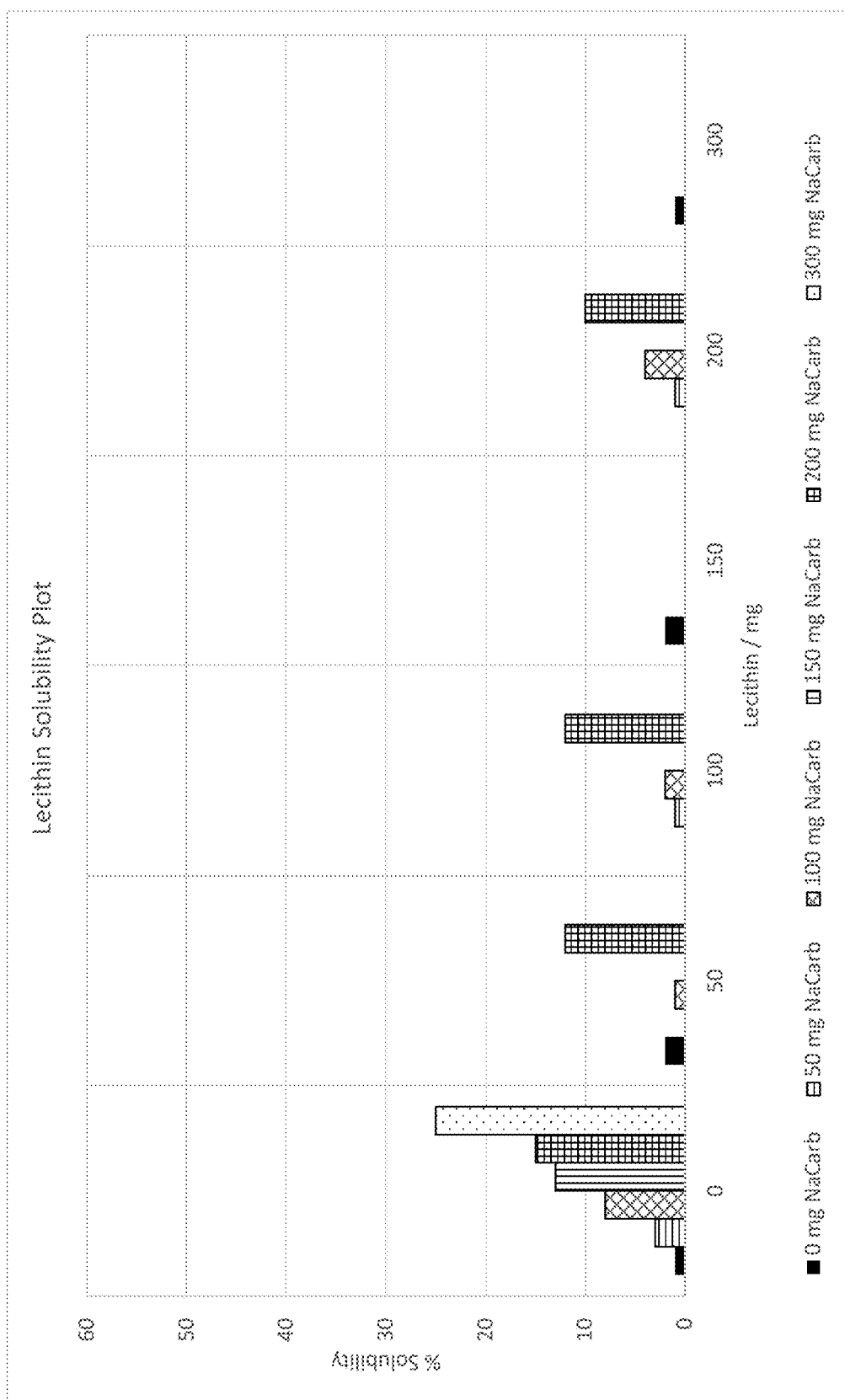
FIG. 9 is a bar graph showing % solubility v amount of lecithin surfactant.
Figure 10:
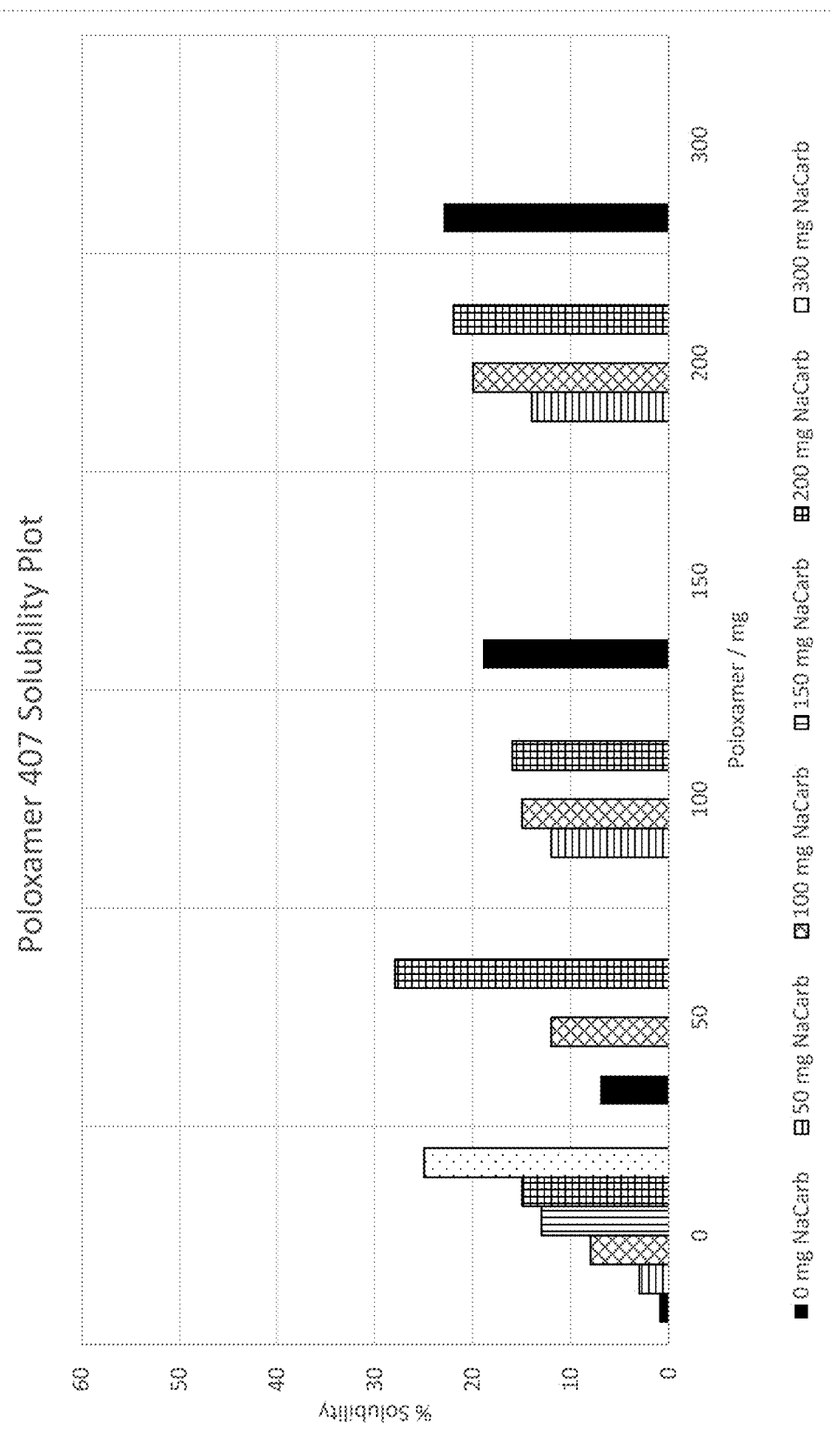
FIG. 10 is a bar graph showing % solubility v amount of poloxamer 407 surfactant.
Figure 11:
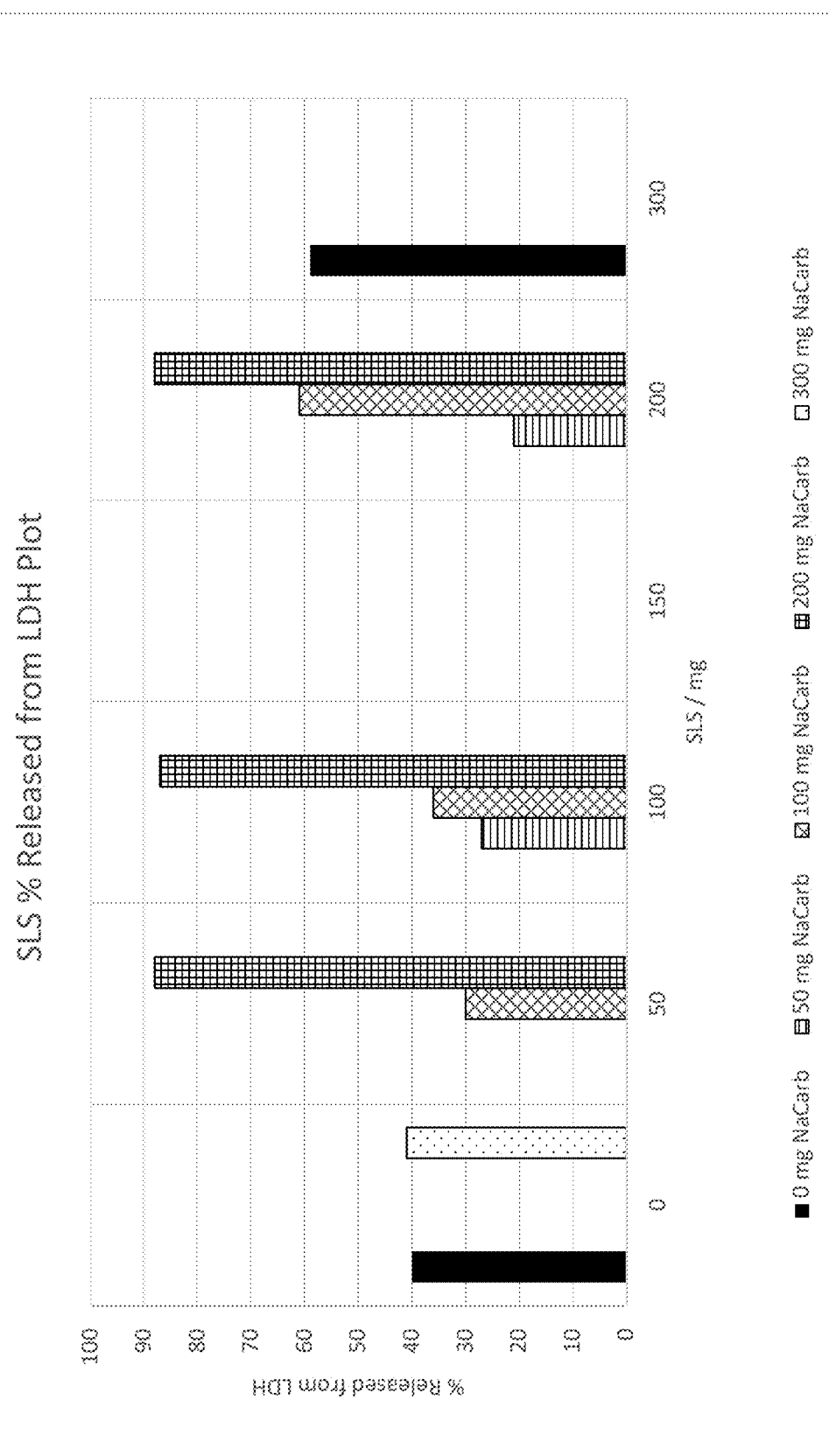
FIG. 11 is a bar graph showing % released v amount of sodium lauryl sulfate (SLS) surfactant.
Figure 12:
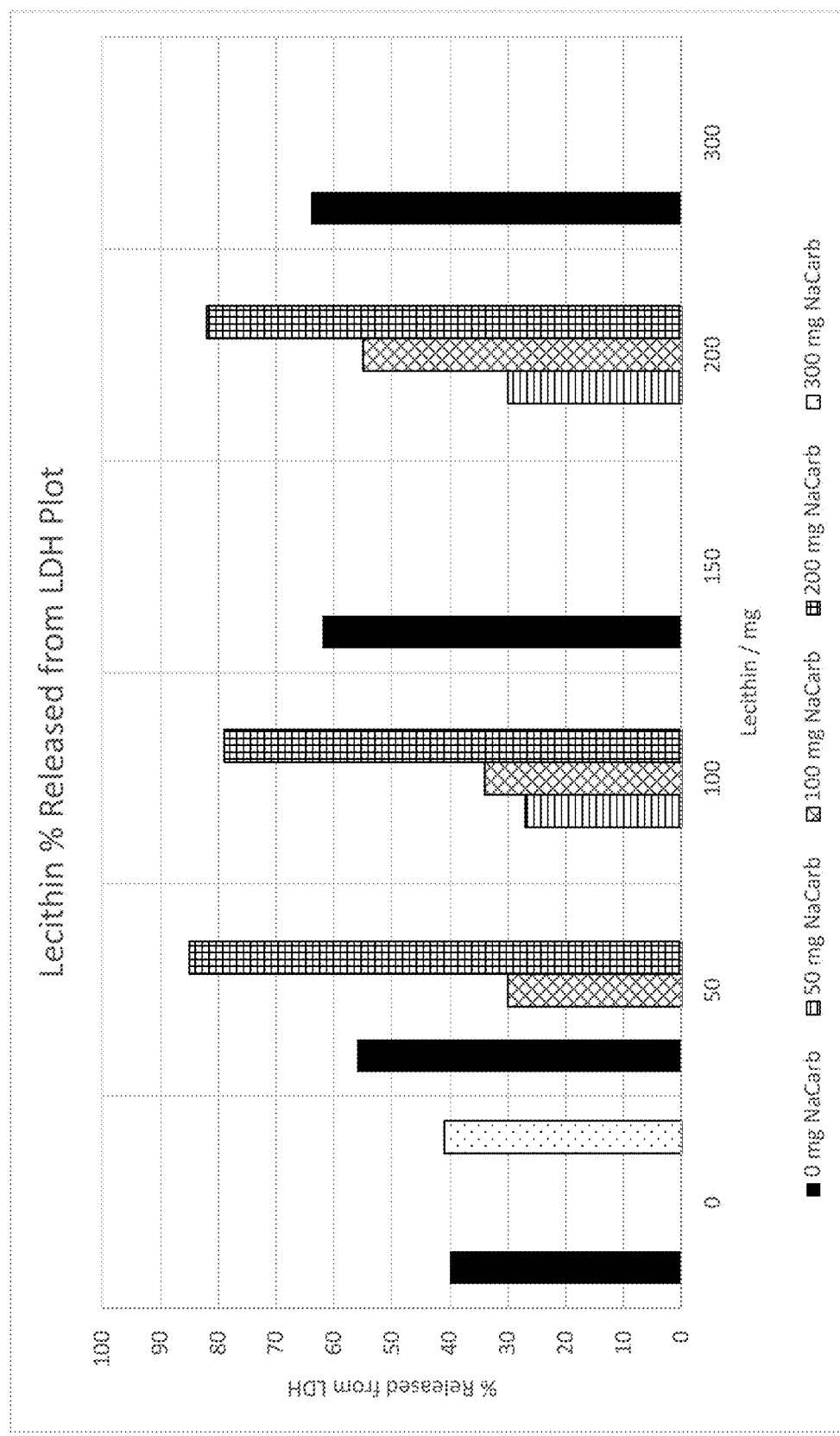
FIG. 12 is a bar graph showing % released v amount of lecithin surfactant.
Figure 13:
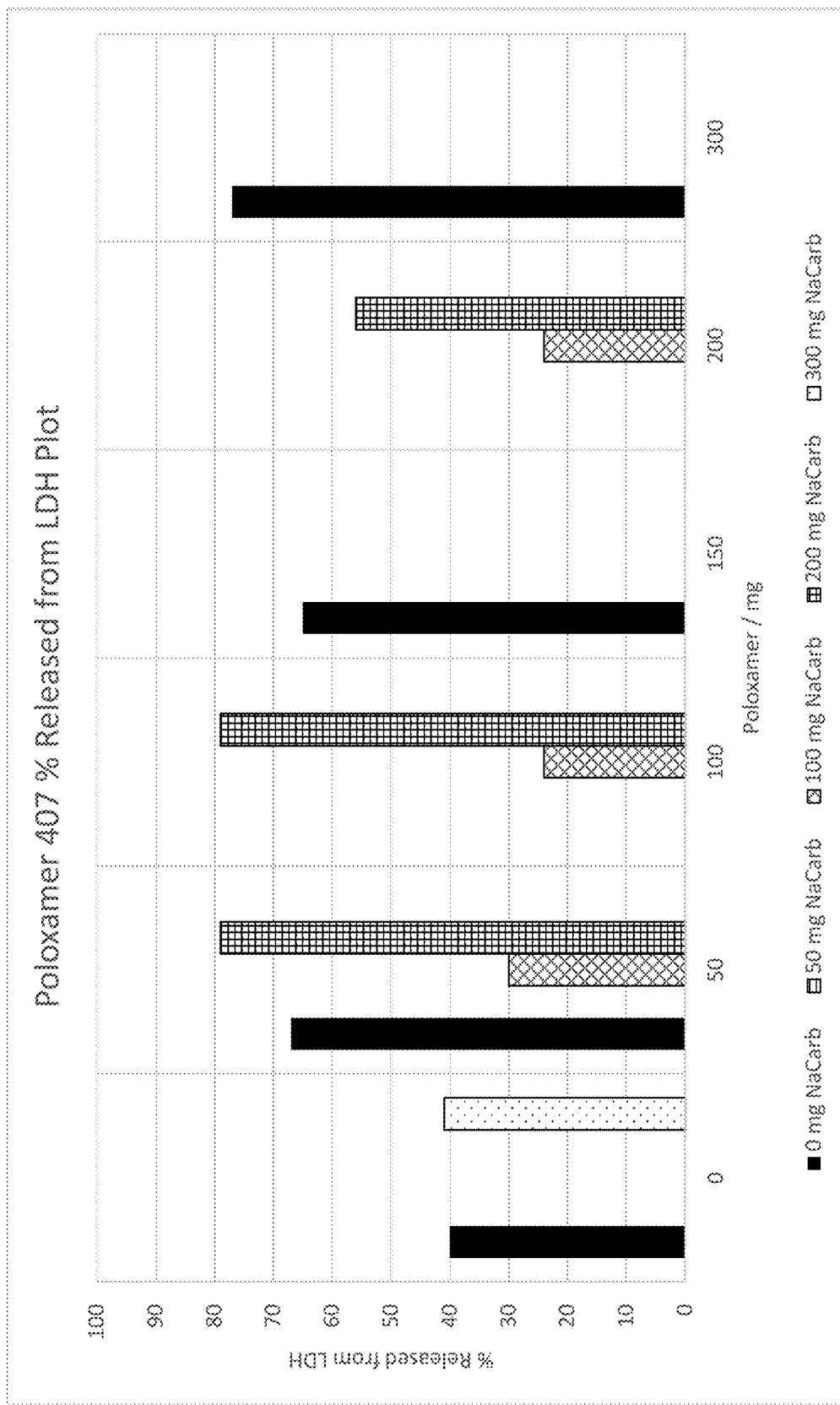
FIG. 13 is a bar graph showing % released v amount of poloxamer 407 surfactant.
Figure 14:
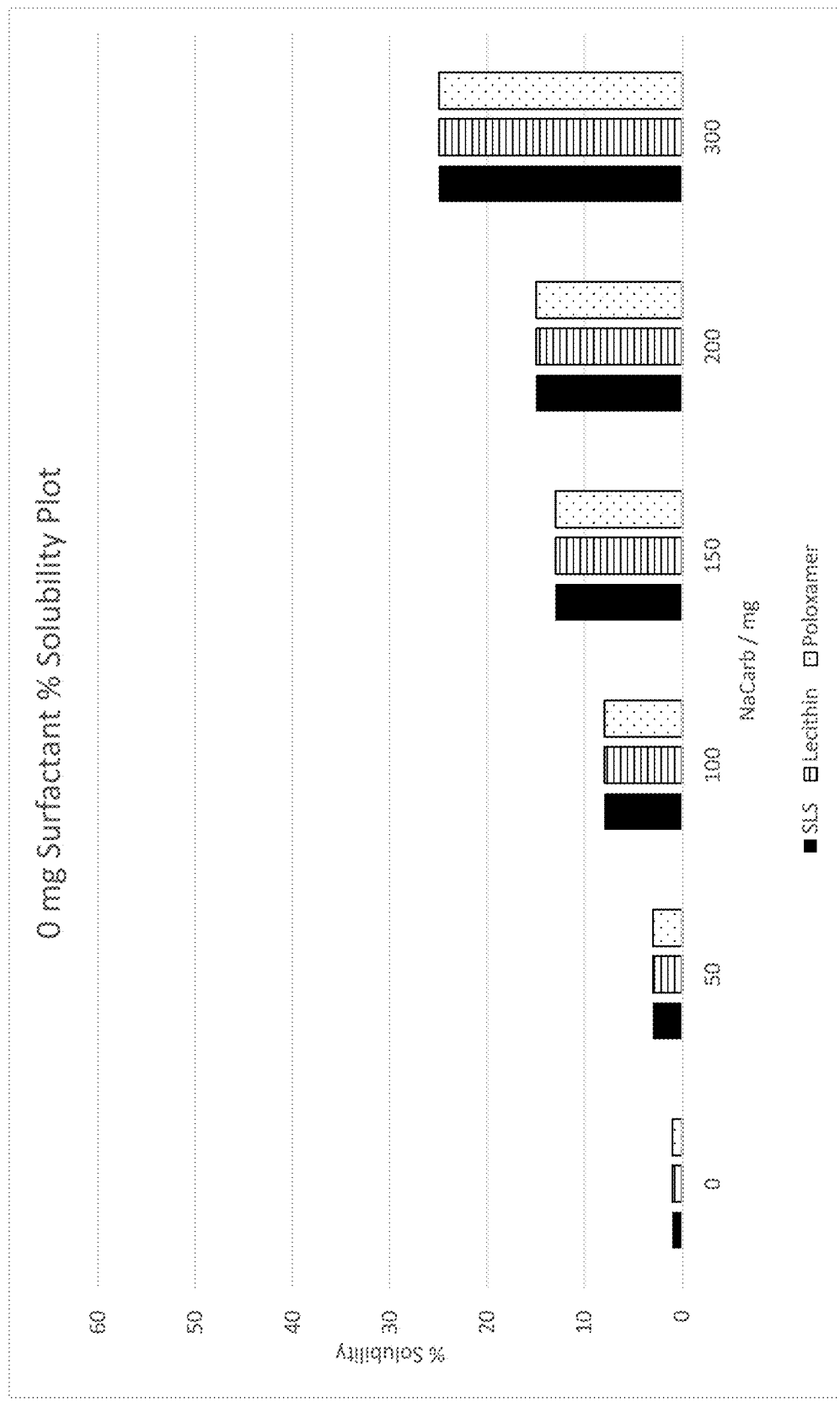
FIG. 14 is a graph showing the % solubility for 0 mg surfactant v amount of sodium carbonate.
Figure 15:
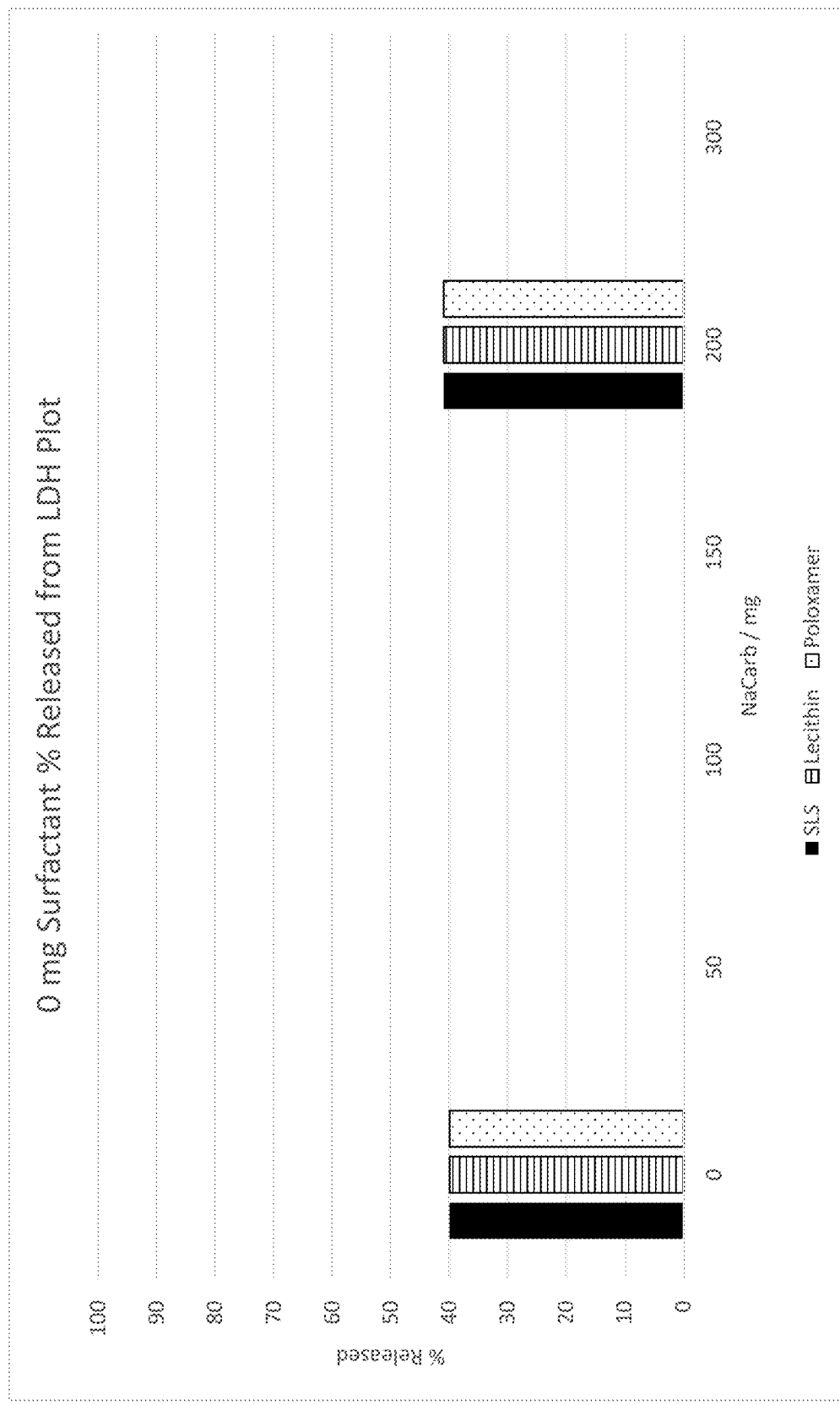
FIG. 15 is a graph showing % release for 0 mg surfactant v amount of sodium carbonate.
Figure 16:
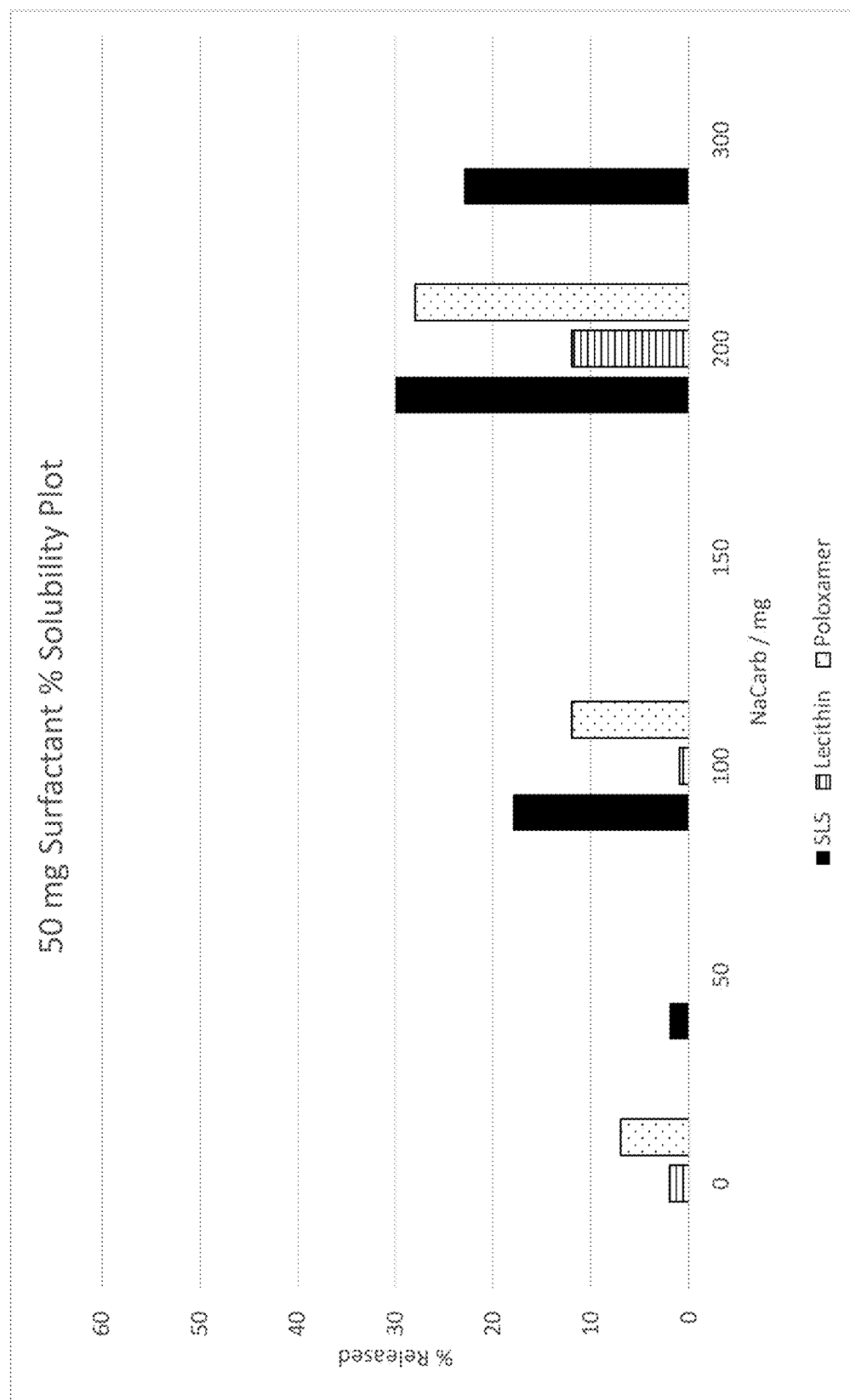
FIG. 16 is a graph showing the % solubility for 50 mg surfactant v amount of sodium carbonate.
Figure 17:
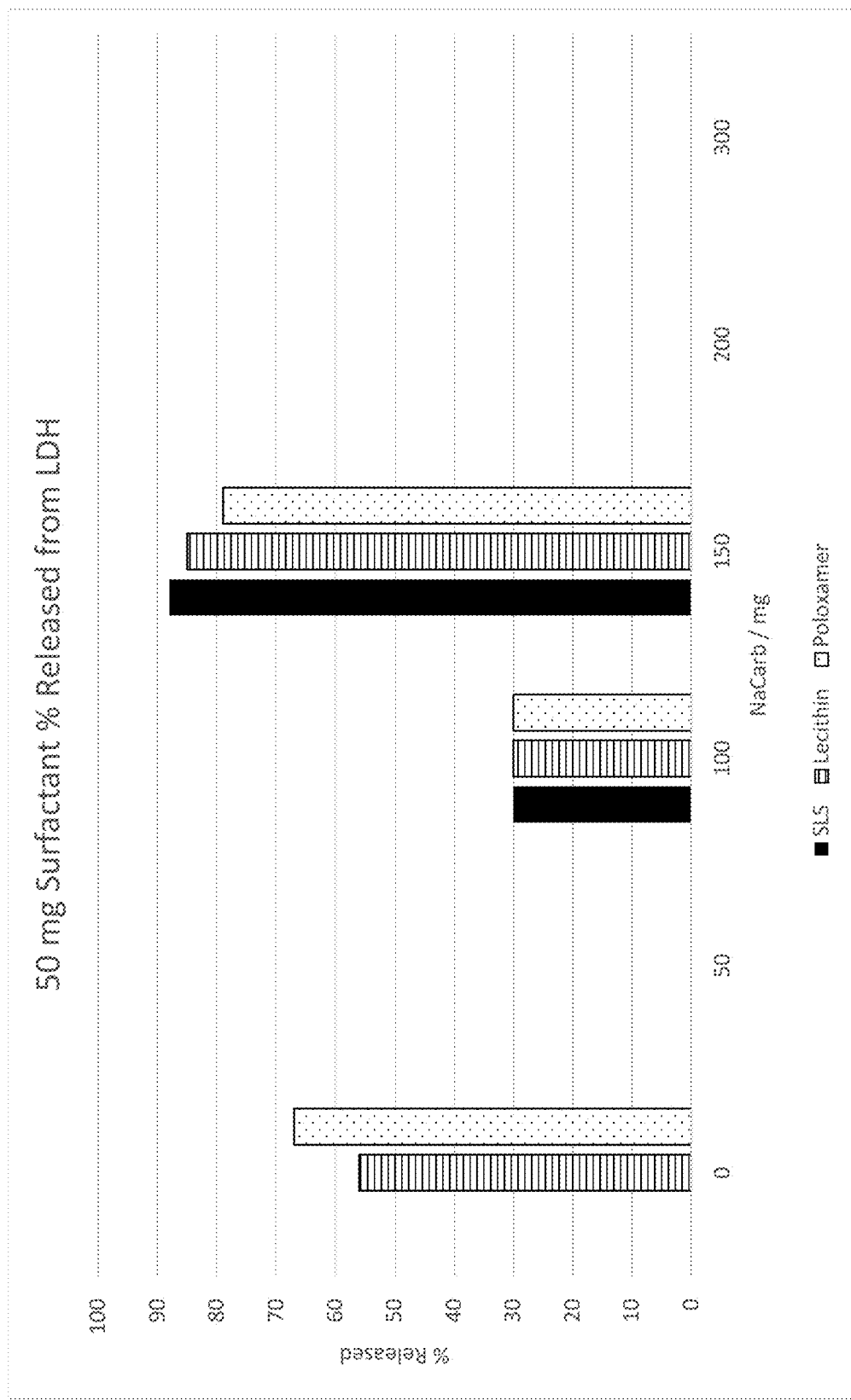
FIG. 17 is a graph showing % release for 50 mg surfactant v amount of sodium carbonate.
Figure 18:
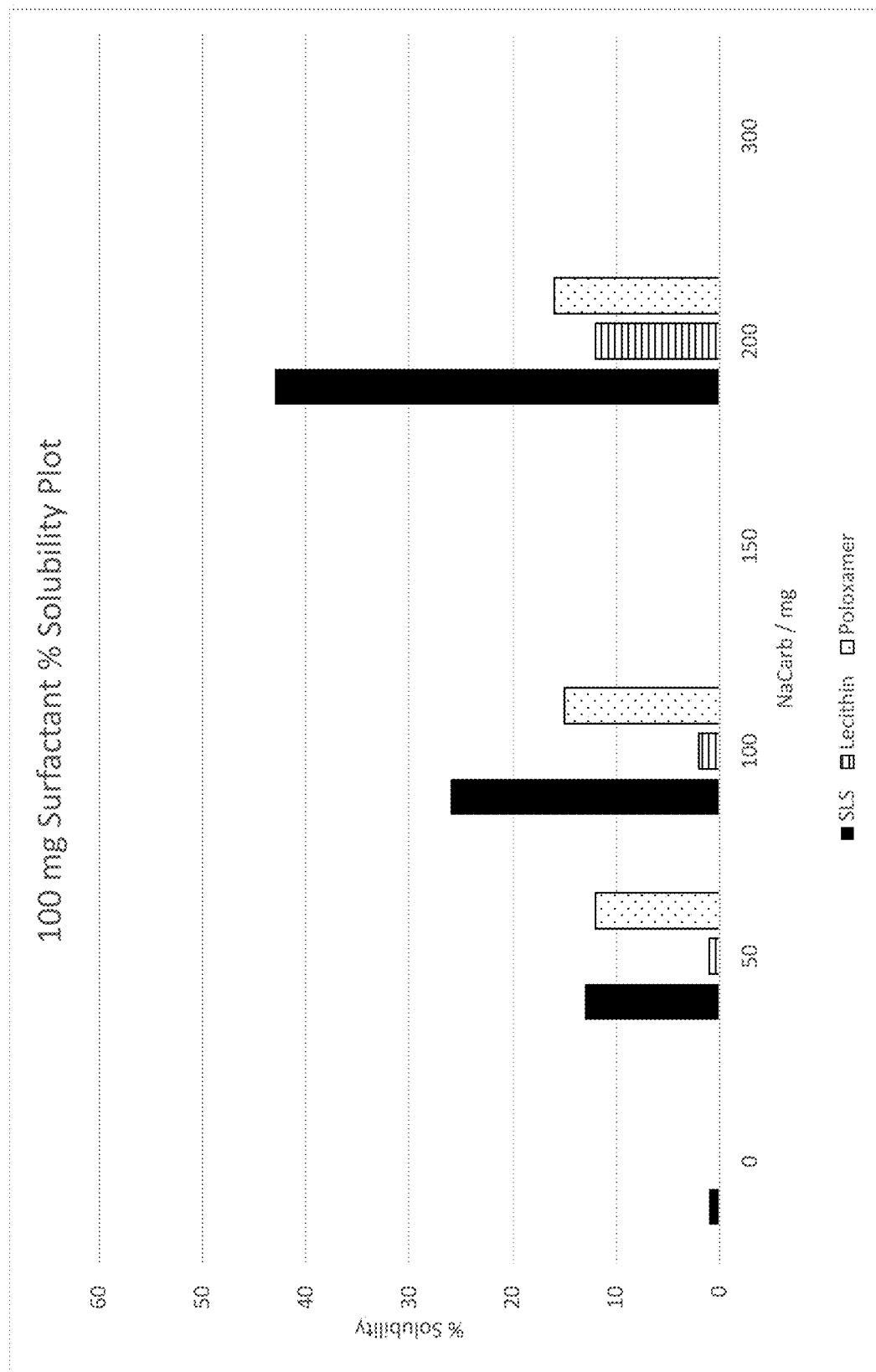
FIG. 18 is a graph showing the % solubility for 100 mg surfactant v amount of sodium carbonate.
Figure 19:
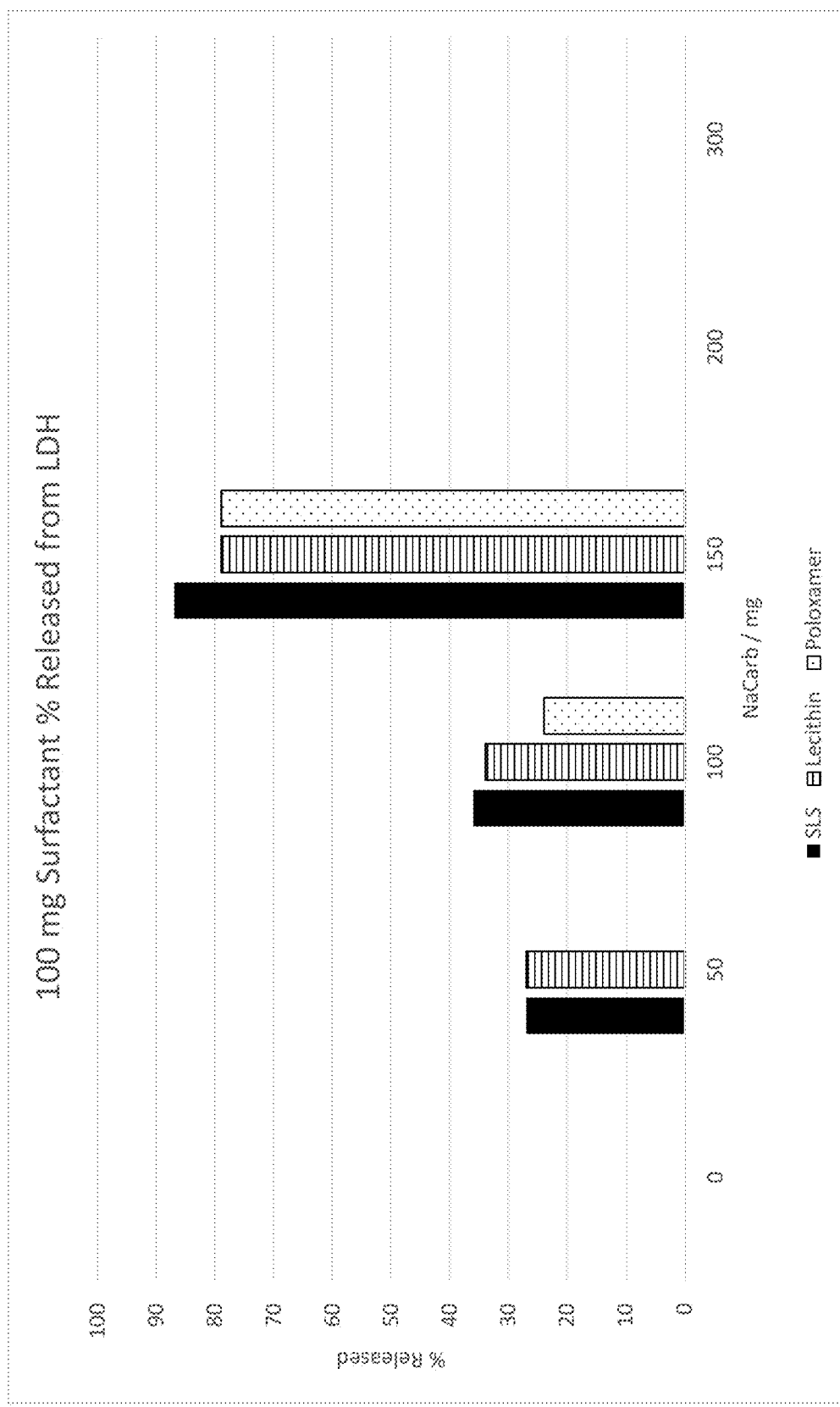
FIG. 19 is a graph showing % release for 100 mg surfactant v amount of sodium carbonate.
Figure 20:
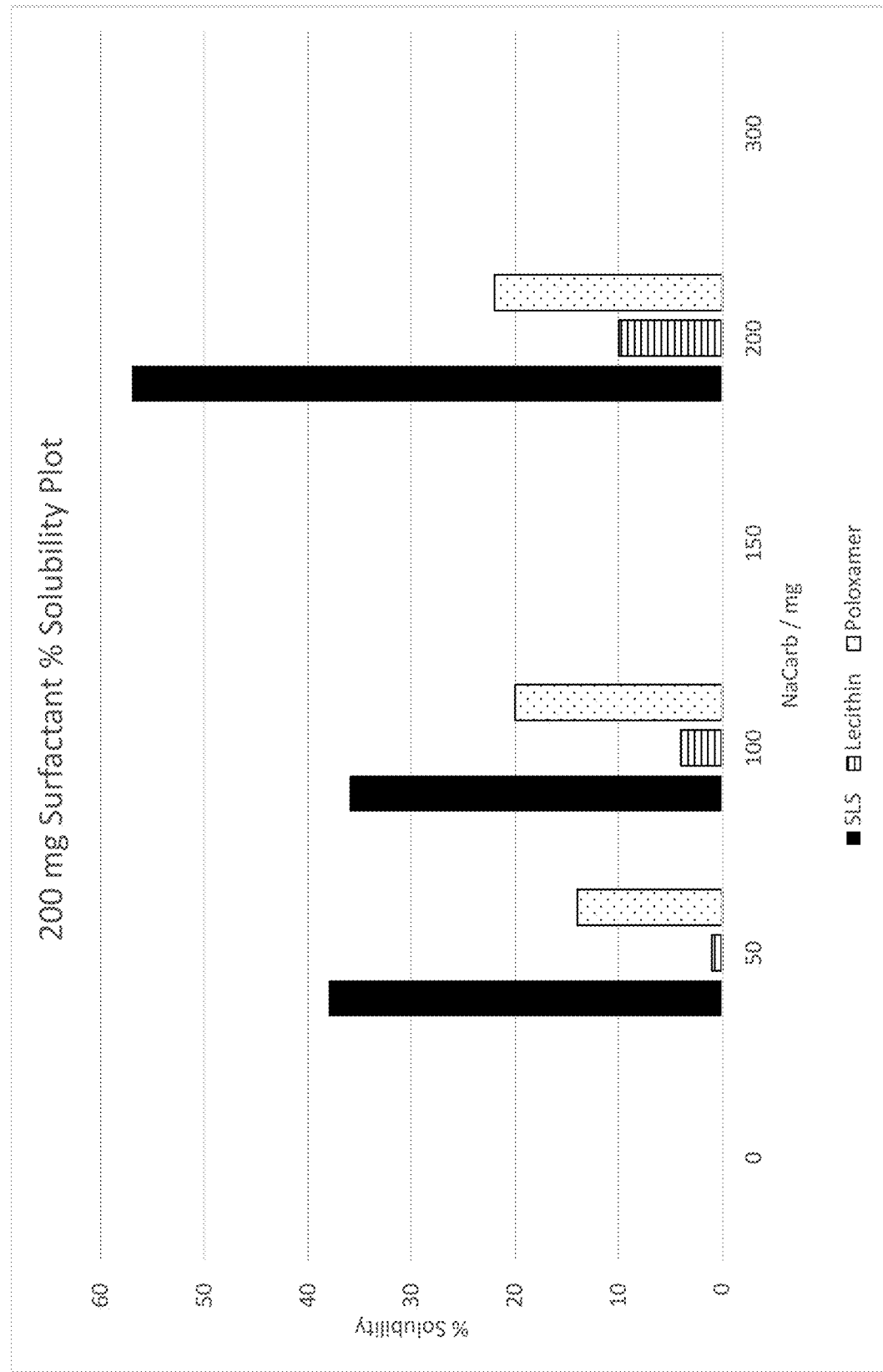
FIG. 20 is a graph showing the % solubility for 200 mg surfactant v amount of sodium carbonate.
Figure 21:
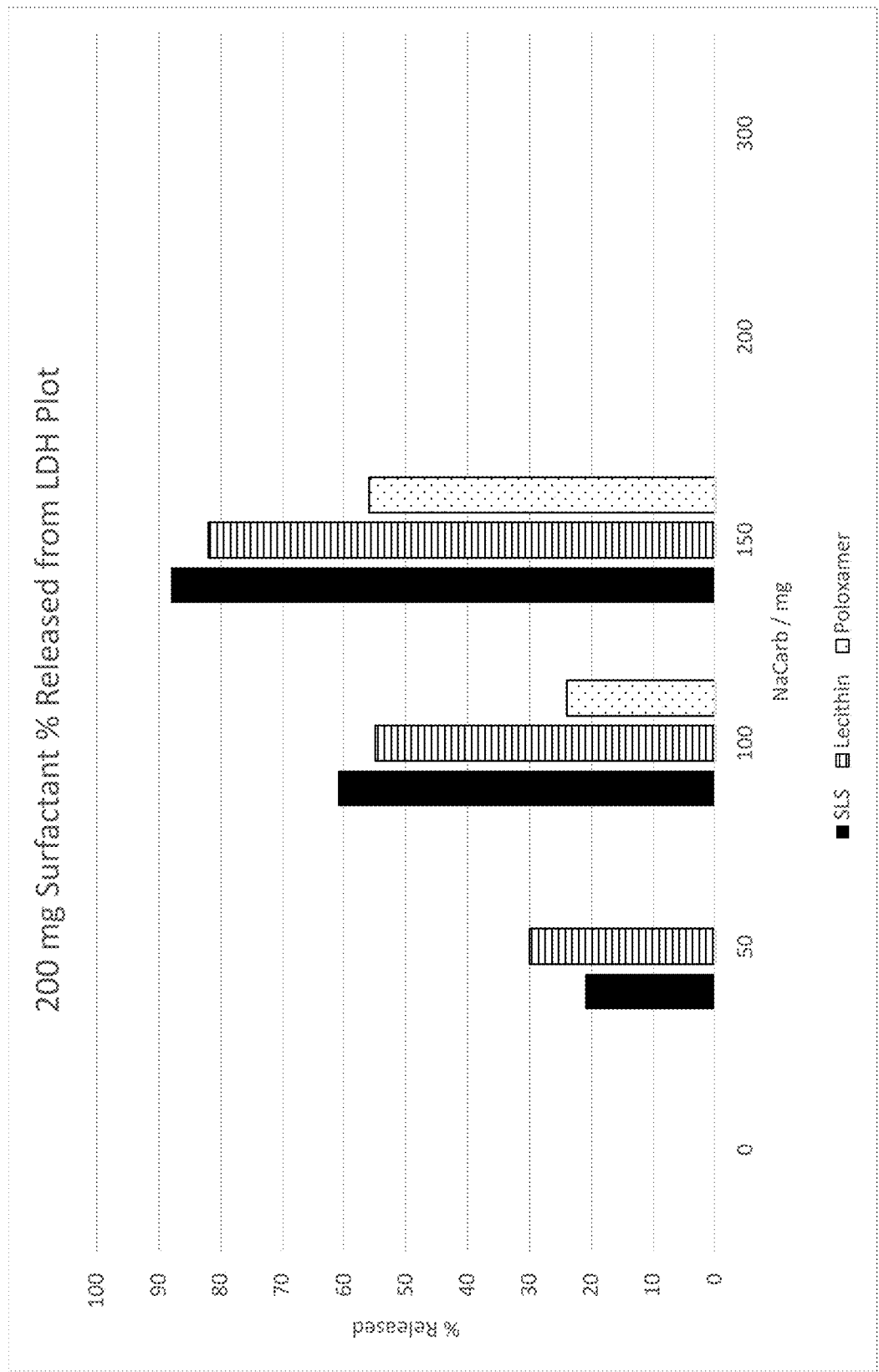
FIG. 21 is a graph showing % release for 200 mg surfactant v amount of sodium carbonate.
Figure 22:
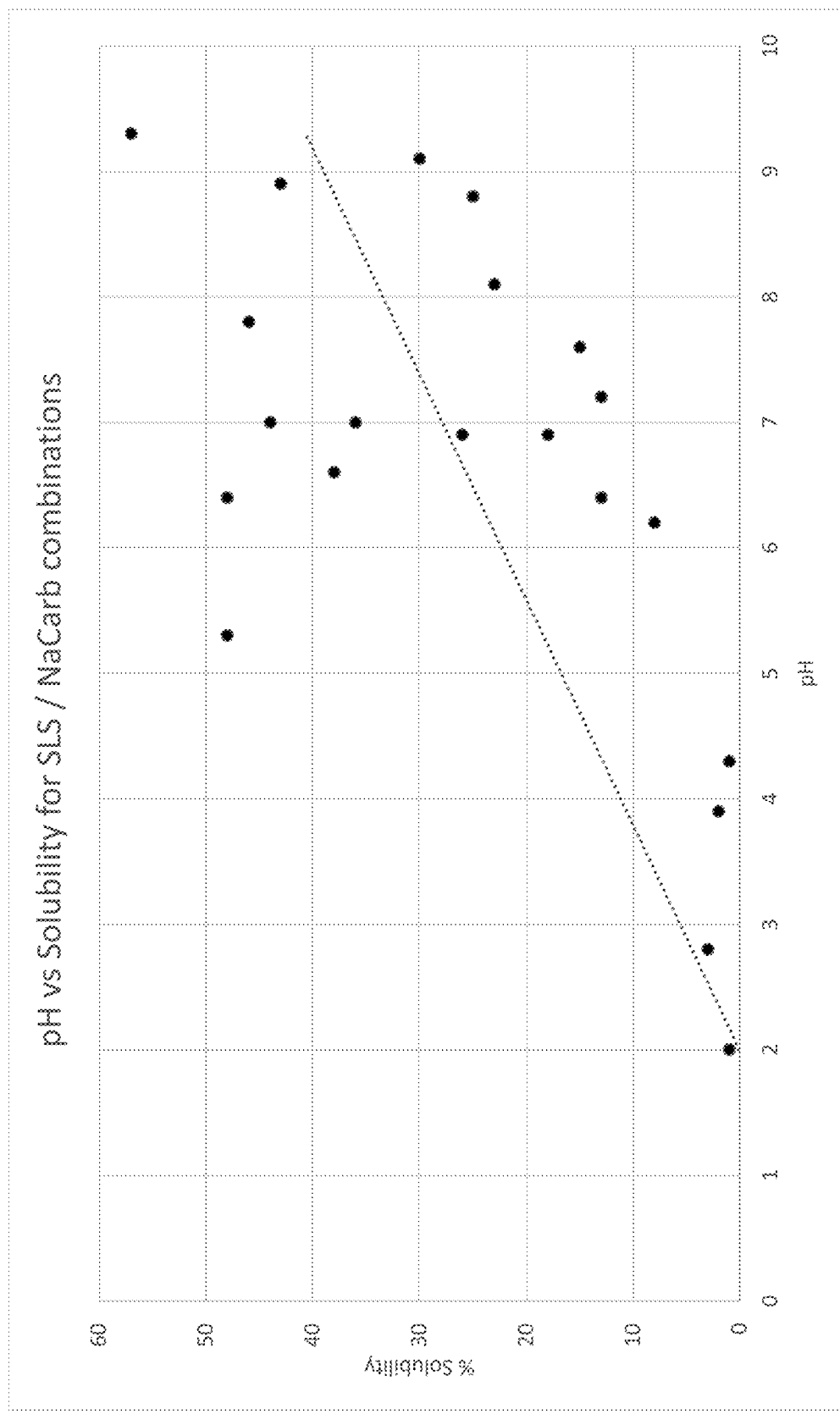
FIG. 22 is a graph showing pH v % solubility in sodium lauryl sulfate (SLS) with sodium carbonate.
Figure 23:
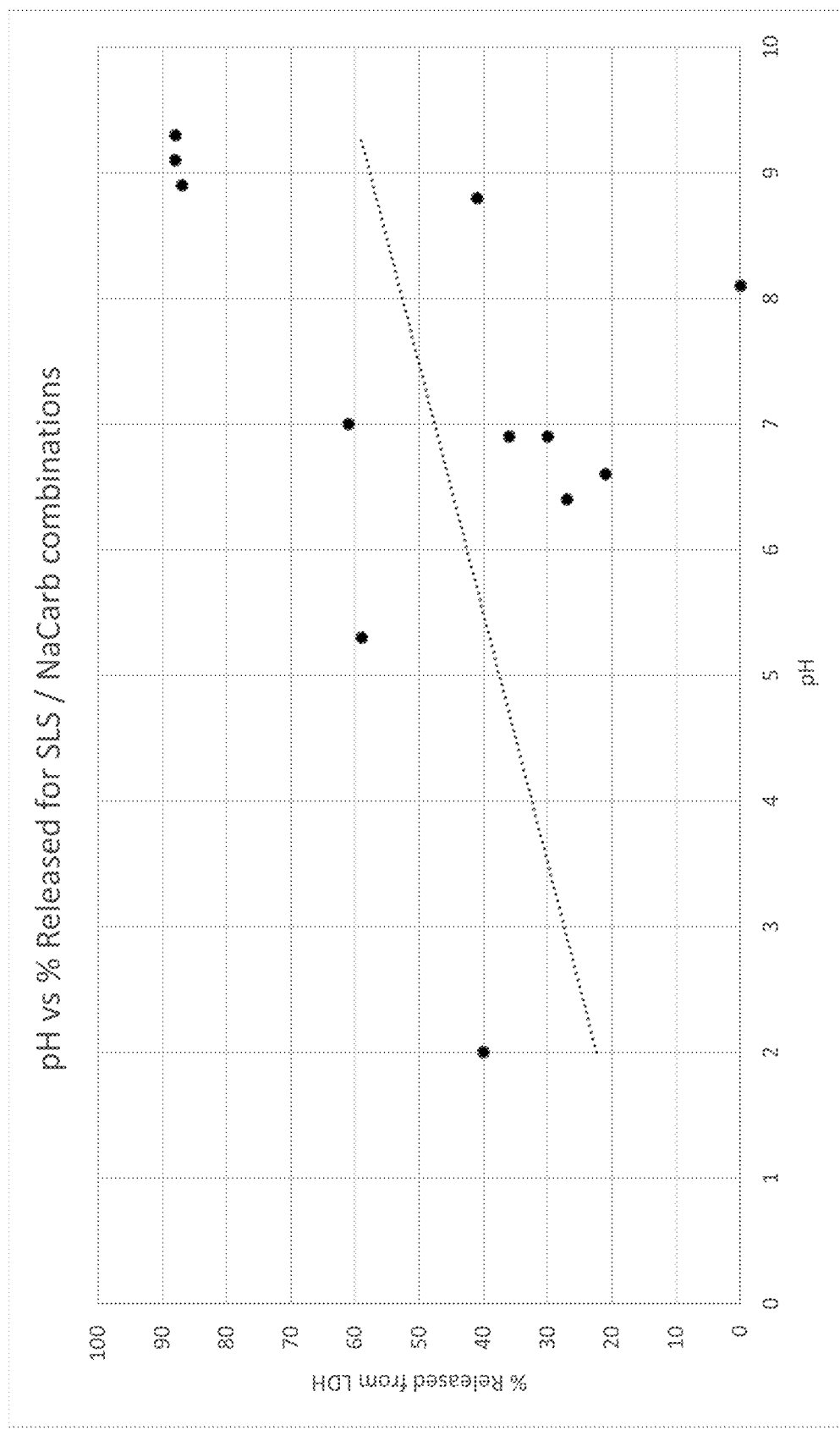
FIG. 23 is a graph showing pH % release in sodium lauryl sulfate (SLS) with sodium carbonate.
Figure 24:
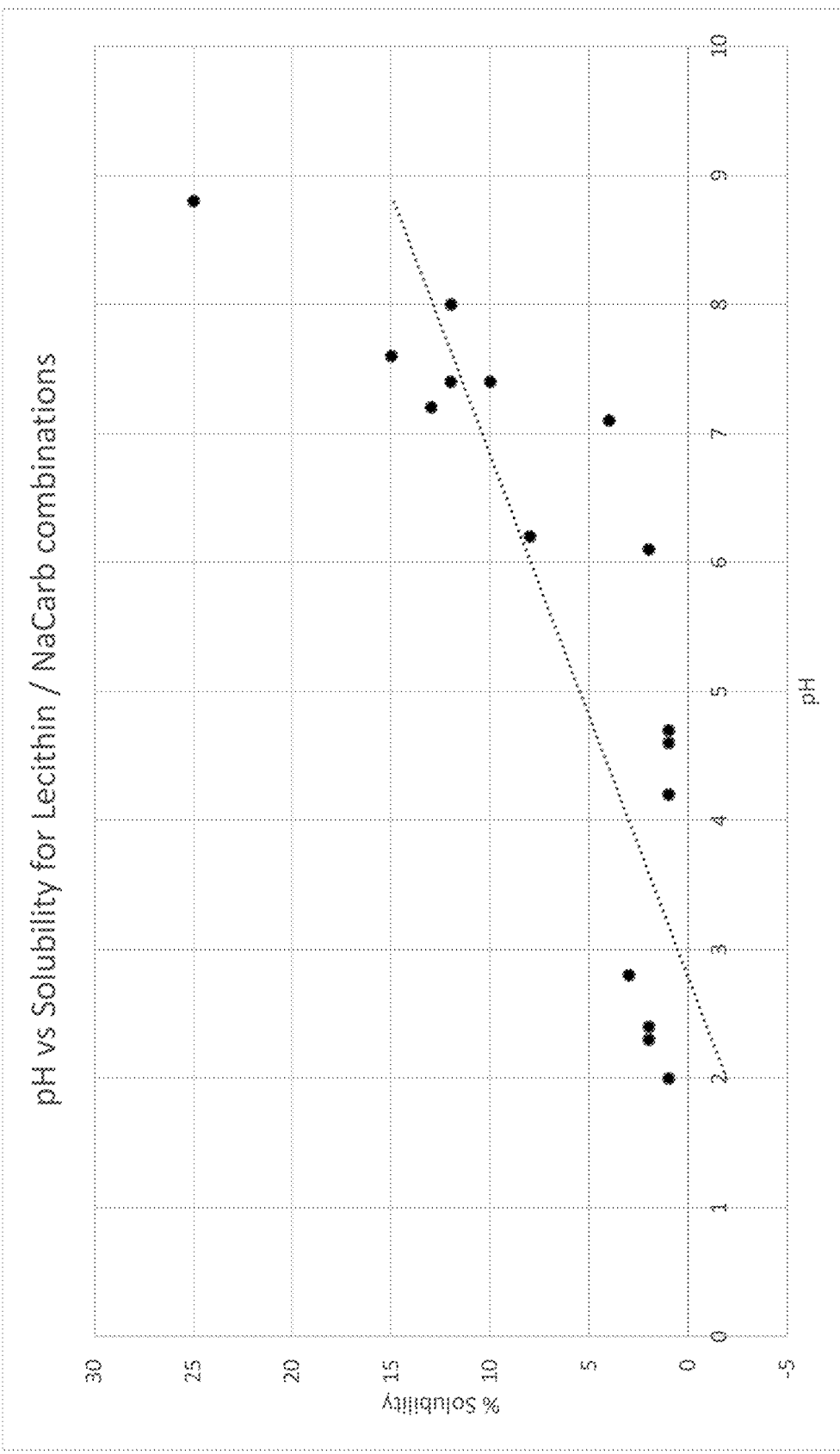
FIG. 24 is a graph showing pH v % solubility in lecithin with sodium carbonate.
Figure 25:
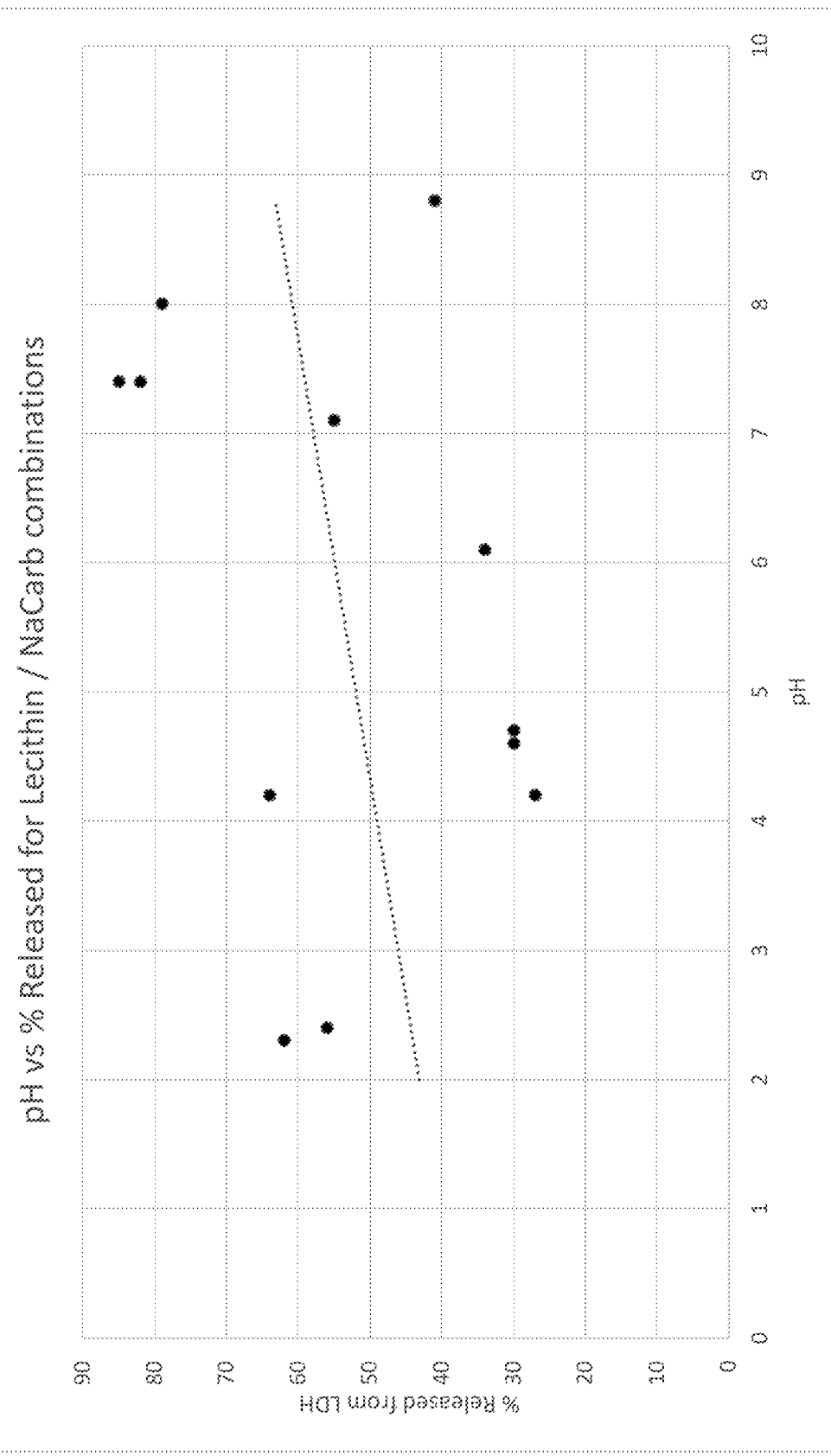
FIG. 25 is a graph showing pH % release in lecithin with sodium carbonate.
Figure 26:
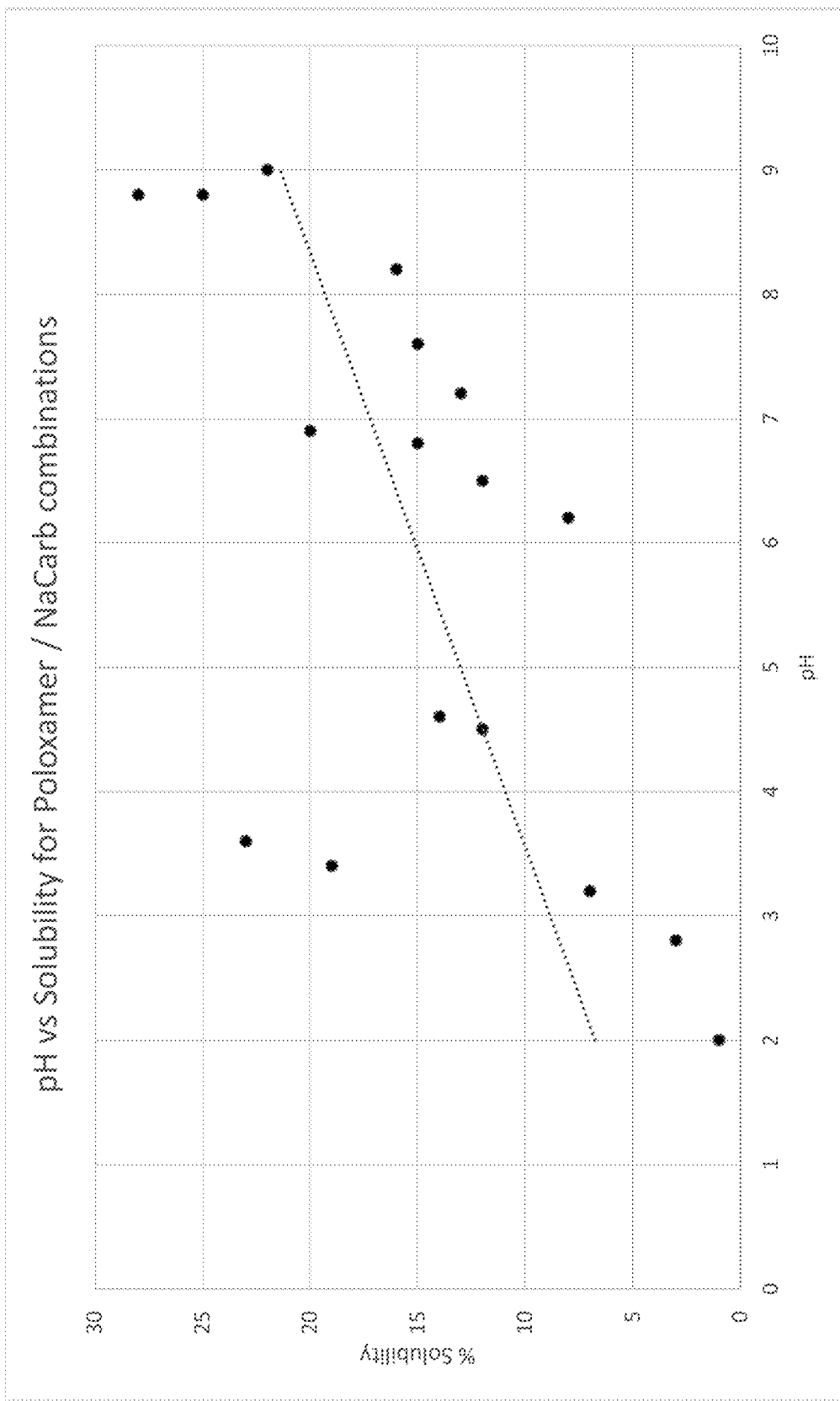
FIG. 26 is a graph showing pH v % solubility in poloxamer 407 with sodium carbonate.
Figure 27:
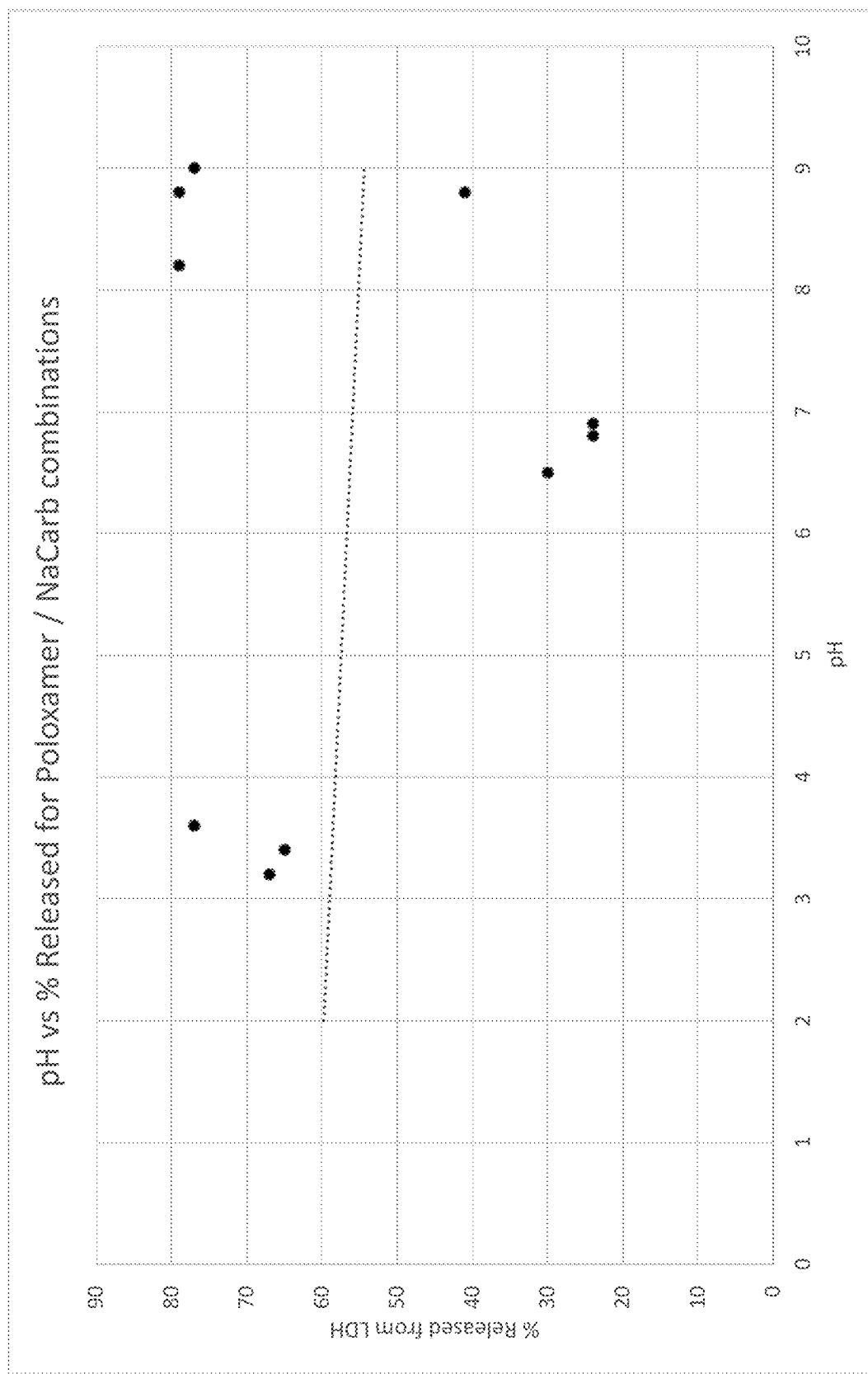
FIG. 27 is a graph showing pH % release in poloxamer 407 with sodium carbonate.

However, in a clinical study to compare the Pharmacokinetic (PK) performance of a tablet formulation of LDH-ibuprofen (400 mg ibuprofen) against the performance of Brufen®, a commercially available tablet formulation containing 400 mg ibuprofen, the LDH-ibuprofen tablet failed to show bioequivalence to the Brufen® product. As illustrated in FIG. 1, the PK results show comparable AUC and time to maximum plasma concentration (Tmax). The rapid ibuprofen absorption in the first hour in the stomach for the LDH-ibuprofen tablet is comparable with the rate of absorption for Brufen®. Following this however, a slower more prolonged ibuprofen release from the LDH-ibuprofen tablet is observed as the remaining ibuprofen ion-exchanges out of the LDH matrix as it travels down the GI tract. This results in a $C_{max}$ for the LDH-ibuprofen tablet being reduced to 65% of that observed with Brufen®.

The differences between the in vitro and in vivo results may be due to the use of a phosphate buffer in the in vitro dissolution testing which may be promoting ion-exchange. This theory was tested and is apparently confirmed as different release rates are obtained depending on which buffer is used and at what concentration. In addition, dissolution testing using FaSSIF and FeSSIF buffers (maleate buffers which are more reflective of the stomach and intestines) showed that these buffers have insufficient buffering capacity to promote ion exchange and hence slowed down the release of the drug from the LDH matrix.

Experiment 2: Testing Different Agents on LDH-Ibuprofen to Determine their Effect on the Amount of Ibuprofen Dissolved Experimental Conditions 400 mg LDH-ibuprofen (equivalent to 200 mg ibuprofen) is added to 0.05M hydrochloric acid (50 ml) with various agents to test their effect in any on the rate of ibuprofen release. The mixture is stirred for 15 minutes and then sampled HPLC for analysis.

TABLE 1

| AGENT | AGENT @ 100 mg | | | AGENT @ 300 mg | | |
|---|---|---|---|---|---|---|
| | pH | DISSOLVED (%) | mg/mL | pH | DISSOLVED (%) | mg/mL |
| NONE (CONTROL) | 2.0 | 1 | 0.04 | 6.1 | 4 | 0.14 |
| MgCO$_3$ | 2.6 | 2 | 0.06 | — | — | — |
| Na(CO$_3$)$_2$ | 6.2 | 8 | 0.33 | — | — | — |
| NaHCO$_3$ | 2.7 | 2 | 0.09 | — | — | — |
| CaCO$_3$ | 2.5 | 1 | 0.05 | 3.6 | 2 | 0.08 |
| Mg(OH)$_2$ | 2.3 | 1 | 0.04 | | | |
| Na$_2$SO$_4$ | 3.3 | 2 | 0.08 | 3.7 | 1 | 0.05 |
| Sodium Lauryl Sulfate | 4.3 | 1 | 0.03 | 5.3 | 48 | 1.91 |
| Ca$_3$(PO$_4$)$_2$ | 3.2 | 1 | 0.04 | 3.7 | 1 | 0.05 |
| CaHPO$_4$ | 3.2 | 1 | 0.03 | 3.6 | 1 | 0.03 |

Looking at the above results, there does not appear to be any linear relationship between pH and solubility, e.g. 100 mg sodium carbonate and 300 mg of magnesium carbonate each give a pH of approximately 6, but sodium carbonate dissolved about 8% ibuprofen, whereas magnesium carbonate only dissolved about 3.5% ibuprofen. Consequently, contrary to the teaching in EP1341556B, the rate of ibuprofen release from the LDH layers is not merely a matter of ensuring that the pH is at a particular level. Also, as the above results demonstrate, the addition of sodium carbonate surprisingly improves the rate of ibuprofen release to a greater extent than would be expected from the results obtained for the carbonates disclosed in EP1341556B. The two calcium phosphate materials, although similar to the chemicals used in a phosphate buffer, gave poor dissolution whereas adding the surface active agent sodium lauryl sulfate dissolved the highest amount of ibuprofen at 47.6%.

The following two test methods have been developed to test the efficacy of the proposed modifier systems according to the present invention. It is particularly instructive to use the two methods in parallel when the modifier system contains a combination of constituents which alter both the solubility and the release of the ibuprofen:

1) Solvent System Method for Determining the Total Amount of Ibuprofen Released from the LDH This method determines the total amount of ibuprofen that is released from the LDH matrix.

Method:

LDH-ibuprofen (200 mg dose of ibuprofen) and modifier agent (where used, in the amounts shown in Table 2), are added to 0.05M HCl (50 mL) and the resulting solution stirred for 15 minutes. After 15 minutes, methanol (50 mL) followed by a 1:1 mixture of methanol and water (150 mL) are added to the stirred LDH-ibuprofen/HCl solution. A sample is then removed for analysis to determine the total amount of ibuprofen (dissolved and undissolved) which is released into the HCl solution. Further dilution is conducted as required.

2) Solubility Method for Determining the Amount of Ibuprofen Dissolved

The solubility method determines how much of the free ibuprofen dissolves in the acid medium. The medium is designed to reflect the conditions found in a fasted human stomach. The difference between the amount determined by method 1 and the amount determined by method 2 is the amount of ibuprofen which formed as a precipitate.

LDH-ibuprofen (200 mg dose of ibuprofen) and modifier agent according to the present invention (where used, in the amounts shown below in Table 2), are added to 0.05M HCl (50 mL) and the resulting solution stirred for 15 minutes. After 15 minutes, a sample is taken for analysis to determine the amount of ibuprofen dissolved in the HCl solution. Further dilution is conducted if required with a standard diluent (acetonitrile:water).

TABLE 2

| SAMPLE | TOTAL AMOUNT OF IBUPROFEN RELEASED FROM THE LDH AS DETERMINED USING THE SOLVENT METHOD | AMOUNT OF IBUPROFEN DISSOLVED AS DETERMINED USING THE SOLUBILITY METHOD |
|---|---|---|
| Ibuprofen free acid | 95% | Negligible |
| LDH-ibuprofen + 300 mg $Na_2CO_3$ | 41% | 26% |
| LDH-ibuprofen + 300 mg SLS | 59% | 48% |

Experiment 3: Testing Modifier Systems According to the Present Invention which Comprise a Range of Compounds with the General Formula MA Together with a Range of Surfactants A composition containing 400 mg LDH-ibuprofen (200 mg dose of ibuprofen), and a modifier system containing 200 mg of a compound with the general formula MA and 200 mg of a surfactant, were mixed together and added to 0.05M HCl (50 mL) and the resulting solution stirred for 15 minutes. Samples of the of the reaction solution were removed and used to determine the amount of ibuprofen released by each of the modifier systems using both the solvent system method and the solubility method described above. The results obtained are detailed below in Table 3a and Table 3b.

As the results in Table 3a show, all of the modifier systems tested affect (increase or decrease) the total amount of ibuprofen released and/or the amount of ibuprofen dissolved, and using this fact it is possible to design a modifier system which will control the amount of active anion released and control the amount of active anion dissolved in the acidic media of the stomach. The modifier system which significantly increases the total amount of ibuprofen released from LDH-ibuprofen, relative to the total amount of ibuprofen released from LDH-ibuprofen in the absence of a modifier system, comprises 200 mg lecithin and 200 mg of one of sodium carbonate, sodium phosphate, disodium hydrogen phosphate, sodium citrate, lithium carbonate and lithium citrate. A modifier system which comprises 200 mg sodium lauryl sulfate and 200 mg sodium carbonate also significantly increases both the total amount of ibuprofen released and the amount of ibuprofen which dissolves. A modifier system which significantly decreases the total amount of ibuprofen released from LDH-ibuprofen, relative to the total amount of ibuprofen released from LDH-ibuprofen in the absence of a modifier system, comprises 200 mg lecithin and 200 mg of one of sodium dihydrogen phosphate, aluminium carbonate and calcium carbonate.

Experiment 4: Determination of the Amount of Ibuprofen Released from LDH-Ibuprofen Compositions by the Addition of Test Modifier Systems According to the Present Invention (Sodium Carbonate and Surfactant) to an LDH-Ibuprofen Material.

A composition containing 400 mg LDH-ibuprofen (200 mg dose of ibuprofen), sodium carbonate and a surfactant in TABLE 3a

| | Surfactant | | | | | | | | | | | |
|---|---|---|---|---|---|---|---|---|---|---|---|---|
| | None | | | Lecithin | | | Poloxamer | | | Sodium lauryl sulfate | | |
| Salt (200 mg) | pH | Solubility Method (%) | Solvent Method (%) | pH | Solubility Method (%) | Solvent Method (%) | pH | Solubility Method (%) | Solvent Method (%) | pH | Solubility Method (%) | Solvent Method (%) |
| None | 2.0 | 1 | 40 | | | | | | | | | |
| Sodium carbonate | | | | 7.4 | 3 | 82 | 9.0 | 6 | 56 | 9.3 | 57 | 88 |
| Sodium Bicarbonate | | | | 4.9 | 4 | 43 | | | | | | |
| Sodium sulfate | | | | 2.4 | 3 | 56 | | | | | | |
| Sodium nitrate | | | | 2.1 | 4 | 64 | | | | | | |
| Sodium dihydrogen phosphate | | | | 3.9 | 8 | 22 | | | | | | |
| Sodium phosphate | | | | 7.3 | 30 | 99 | | | | | | |
| Sodium hydroxide | | | | 12.1 | 33 | 63 | | | | | | |
| Sodium chloride | | | | 2.8 | 2 | 51 | | | | | | |
| Disodium hydrogen phosphate | | | | 5.8 | 13 | 95 | | | | | | |
| Sodium citrate | | | | 4.3 | 1 | 95 | | | | | | |
| Magnesium carbonate | | | | 2.9 | 2 | 44 | | | | | | |
| Aluminium carbonate | | | | 2.1 | 1 | 11 | | | | | | |
| Calcium carbonate | | | | 4.9 | 0 | 26 | | | | | | |
| Lithium citrate | | | | 5.6 | 14 | 94 | | | | | | |

TABLE 3b

| | Surfactant | | | | | |
|---|---|---|---|---|---|---|
| | Benzalkonium chloride | | | Diotadecyl-dimethylammonium chloride | | |
| Salt | pH | Solubility Method | Solvent Method | pH | Solubility Method | Solvent Method |
| Sodium carbonate | 4.0 | 7 | 50 | 6.7 | 2 | 36 | different ratios were mixed together and added to 0.05M HCl (50 mL) and the resulting solution stirred for 15 minutes. Samples of the of the reaction solution were removed and used to determine the amount of ibuprofen released by each of the sodium carbonate/surface active agent combinations using both the solvent system method and the solubility method described above. The results obtained are detailed in FIG. 28.

Conclusion

The results presented in FIG. 28 highlight many interesting features of the relationship between sodium carbonate and a surfactant, and the resulting effect this combination has on the % release of ibuprofen from an LDH matrix and the % solubility of the released ibuprofen in an acidic medium. Some of these features include:

The presence of sodium carbonate appears to provide a decrease in the % release of the ibuprofen (41% with sodium carbonate v 65% without sodium carbonate), but the amount of released ibuprofen which then dissolves in an acid medium is increased from 1% (when no sodium carbonate is present) to 25% (when 300 mg sodium carbonate is present).

For a particular amount of sodium carbonate, the total amount of ibuprofen released does not appear to be influenced by either the choice of surfactant or the amount of surfactant (in the range 50 mg to 300 mg). However, the choice of surfactant does appear to influence the solubility of the released active anion and there is a wide variation in % solubility over the range of surfactants tested. This suggests that not all of the surfactants act to solubilise the released ibuprofen. Also the presence of sodium carbonate appears to act in a similar way with all surfactants because (apart for a couple of exceptions 200 mg Sodium Lauryl Sulfate (SLS) and 200 mg lecithin) the % release is of a similar order of magnitude for a given level of sodium carbonate.

The addition of <100 mg sodium carbonate appears to cause a decrease in the % release, relative to the % release observed for 0 mg sodium carbonate, whereas the addition of >100 mg sodium carbonate appears to increase % release and with 200 mg sodium carbonate % release of 77 to 88% is observed. This provides the benefit that the amount of ibuprofen release can be controlled, and not just increased, by using the modifier systems of the present invention.

Experiment 5: Determination of the Amount of Active Anion Released from LDH-Active Anion Compositions by the Addition of Test Modifier Systems According to the Present Invention (Sodium Carbonate and Surfactant) to an LDH-Active Anion Material This Experiment is analogous to Experiment 4 above except that it tests the effect of the modifier systems according to the present invention (which comprise either lecithin or poloxamer in combination with sodium carbonate) on LDH-active anion materials, where the active anion is either naproxen, ketorolac, diclofenac or atorvastatin.

A composition containing LDH-active anion (containing a 200 mg dose of the active anion), sodium carbonate and a surfactant in different ratios were mixed together and added to 0.05M HCl (50 mL) and the resulting solution stirred for 15 minutes. Samples of the reaction solution were removed and used to determine the amount of active anion released by each of the sodium carbonate/surface active agent combinations using both the solvent system method and the solubility method described above. The results obtained are detailed in FIG. 29.

The invention claimed is:

1. A composition comprising: i) one or more layered double hydroxide (LDH)-active anion materials comprising an LDH matrix intercalated with an active anion, and ii) a modifier system comprising a) a surfactant, in combination with sodium carbonate, wherein the active anion is ibuprofen or naproxen,
    wherein when the active anion is ibuprofen, the surfactant is selected from poloxamer, lecithin, and sodium lauryl sulfate, and the composition has a weight ratio 1:1:0.25 to 1:1:1 (LDH matrix:sodium carbonate:surfactant);
    wherein when the active anion is naproxen, the surfactant is lecithin or poloxamer, and when the surfactant is lecithin, the composition has a weight ratio of 8:5:5 (LDH matrix:sodium carbonate:surfactant) and when the surfactant is poloxamer, the composition has a weight ratio of 8:5:1.25 to 8:5:5 (LDH matrix:sodium carbonate:surfactant).

2. The formulation according to claim 1, in a form selected from dry granules, tablets, caplets, orally disintegrating tablets, orally disintegrating granules, lozenges, films, capsules, powders, effervescent formulations and buccal and sub-lingual formats.

3. The composition according to claim 1, comprising ibuprofen in an amount of 200 mg and sodium carbonate in an amount of 200 mg.

4. The composition according to claim 3, wherein the surfactant is present in an amount of 50 mg, 100 mg, or 200 mg.

5. The composition according to claim 1, wherein the active anion is naproxen.

6. The composition according to claim 5, wherein weight ratio of naproxen:surfactant is 1:1.

7. The composition according to claim 5, wherein the surfactant is lecithin.

8. The composition according to claim 7, comprising the LDH matrix in an amount of 400 mg.

9. The composition according to claim 7, comprising naproxen in an amount of 250 mg.

10. The composition according to claim 7, comprising lecithin in an amount of 250 mg.

11. The composition of claim 5, wherein the surfactant is poloxamer.

12. The composition of claim 11, comprising the LDH matrix in an amount of 400 mg.

13. The composition of claim 11, comprising naproxen in an amount of 250 mg.

14. The composition of claim 12, comprising poloxamer in an amount from 62.5 mg to 250 mg.

* * * * *